(12) United States Patent
Hatton et al.

(10) Patent No.: US 7,795,041 B2
(45) Date of Patent: Sep. 14, 2010

(54) MULTI-POLYMER-COATED MAGNETIC NANOCLUSTERS

(75) Inventors: T. Alan Hatton, Sudbury, MA (US); Daniel I. C. Wang, Newton, MA (US); Paul Laibinis, Houston, TX (US); Andre Ditsch, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 597 days.

(21) Appl. No.: 11/053,678

(22) Filed: Feb. 9, 2005

(65) Prior Publication Data

US 2005/0215687 A1 Sep. 29, 2005

Related U.S. Application Data

(60) Provisional application No. 60/543,271, filed on Feb. 11, 2004.

(51) Int. Cl.
*G01N 33/553* (2006.01)
*G01N 33/543* (2006.01)
*G01N 33/24* (2006.01)

(52) U.S. Cl. .................. 436/526; 436/523; 436/532; 436/533; 436/84

(58) Field of Classification Search .......... 436/526, 436/532, 533, 84; 435/157; 977/773
See application file for complete search history.

(56) References Cited

U.S. PATENT DOCUMENTS

| 4,560,655 A | 12/1985 | Baker et al. |
| 4,657,866 A | 4/1987 | Kumar et al. |
| 4,767,704 A | 8/1988 | Cleveland et al. |
| 4,927,762 A | 5/1990 | Darfler et al. |
| 5,122,469 A | 6/1992 | Mather et al. |
| 5,395,688 A | 3/1995 | Wang et al. |
| 5,667,924 A * | 9/1997 | Ziolo .................... 430/39 |
| 6,133,047 A | 10/2000 | Elaossari et al. |
| 6,623,982 B1 | 9/2003 | Liberti et al. |

FOREIGN PATENT DOCUMENTS

| DE | 198 00 294 A1 | 7/1999 |
| WO | WO87/00195 | 1/1987 |
| WO | WO90/03430 | 4/1990 |
| WO | WO 97/45202 | 12/1997 |

OTHER PUBLICATIONS

Ham et al., (1979) "Media and growth requirements." Meth. Enz., 58: 44.

(Continued)

*Primary Examiner*—Shafiqul Haq
(74) *Attorney, Agent, or Firm*—Pearl Cohen Zedek Latzer, LLP; Mark S. Cohen

(57) ABSTRACT

The present invention relates to multi-polymer-coated magnetic nanoclusters, aqueous magnetic fluids comprising same, and methods of their use in separation procedures. The multi-polymer-coated magnetic nanoclusters comprise a super paramagnetic core, with a first polymer attached thereto, which does not render the first polymer-super paramagnetic particle complex colloidally stable, and a second polymer attached thereto, which stabilizes the complex of multi-polymer-coated magnetic nanoparticles. Methods of use comprise methods of separation, including separation of expressed protein from cells and viruses expressing the same.

44 Claims, 14 Drawing Sheets

OTHER PUBLICATIONS

Figure 1:
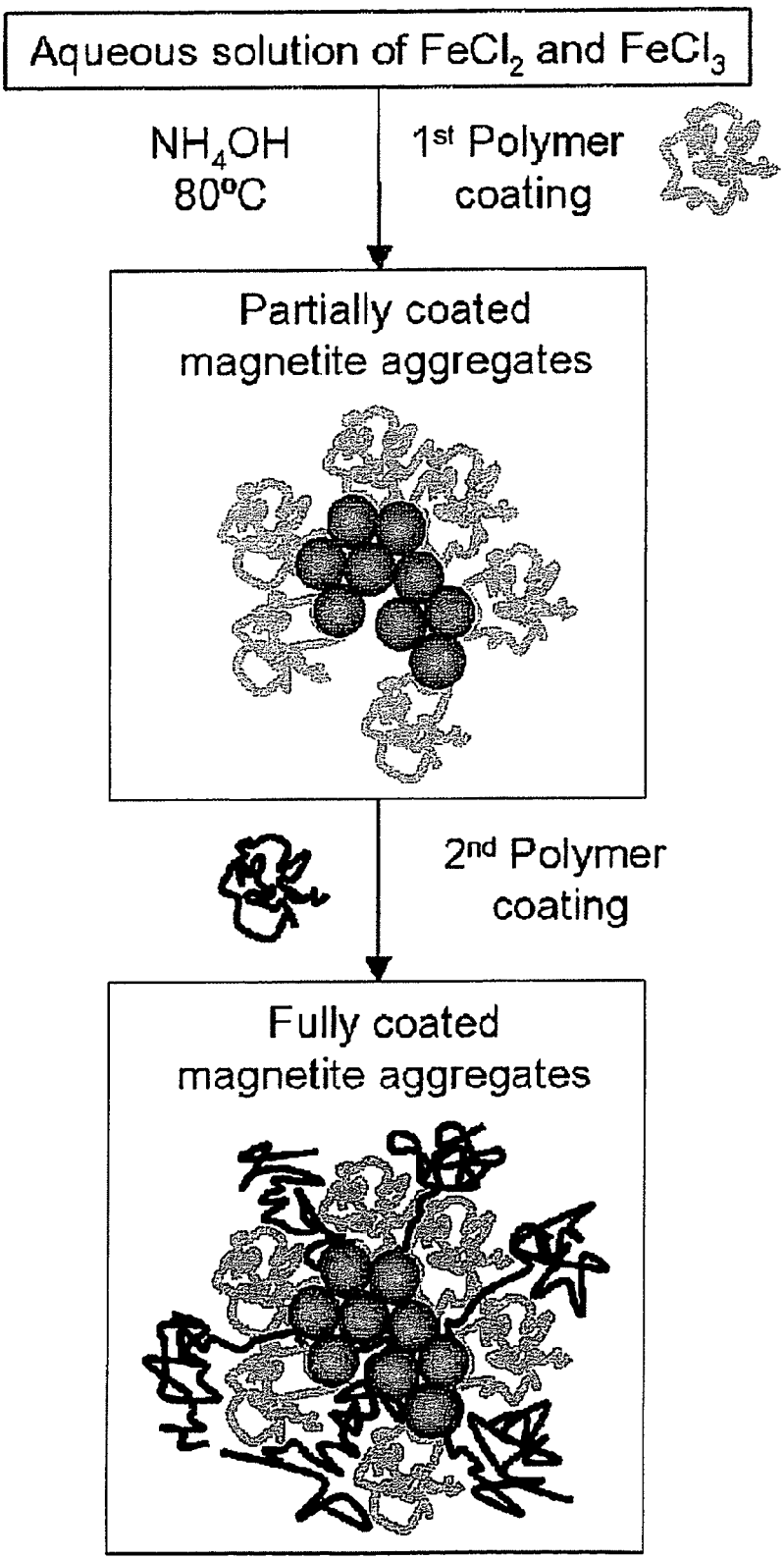

Barnes et al. (1980), "Methods for growth of cultured cells in serum-free medium." Anal. Biochem., 102: 255.

Feuser, J., J. Walter, M.R. Kula, and J. Thommes, *Cell/adsorbent interactions in expanded bed adsorption of proteins*. Bioseparation, 1998. 8(1-5): p. 99-109.

Liberti, P.A.R., Galla Candra; Terstappen; Leon W., Increased Separation efficiency via controlled aggregation of magnetic nanoparticles. 2003.

Supplementary European Search Report issued Mar. 4, 2009.

\* cited by examiner

MULTI-POLYMER-COATED MAGNETIC NANOCLUSTERS

CROSS-REFERENCE TO RELATED APPLICATION

This Application claims priority of U.S. Provisional Application Ser. No. 60/543,271, filed on Feb. 11, 2004, which is hereby incorporated in its entirety.

FIELD OF THE INVENTION

This invention provides compounds and methods for use in protein purification. This invention provides multi-polymer-coated aqueous magnetic fluids, which are useful in ion-exchange purification of proteins from fermentation or any charge or affinity based separation, with one of the embodiments useful for separation of hydrophobic materials from aqueous media. The method of production is useful for the production of the fluids described, as well as for the synthesis of controlled size magnetic nanoparticles with stability in high ionic strength environments for a wide range of separations.

BACKGROUND OF THE INVENTION

Separation of substances of interest from complex solutions has been accomplished via a variety of methods. Some applications include separation of biological substances of interest from a sample, such as, for example, purification of proteins from complex media such as fermentation broth. Such separations have been accomplished, among others, via cell clarification followed by column chromatography and the use of a fluidized bed of chromatographic media. These techniques suffer limitations, however, such as an inability to handle particulate matter and poor mass transfer, in the former, and short contact time, low capacity loading of the resin in the latter.

Magnetic separation is another means by which complex separations may be accomplished. In this context, biologically active magnetic particles in aqueous solution, termed magnetic fluids, have found particular use. The application of high gradient magnetic separation (HGMS), which uses a magnetic field to separate magnetic particles from suspension has been exploited such that when these particles are attached to biological materials of interest (e.g., cells, drugs), the material of interest or target material may thereby be separated from other materials not bound to the magnetic particles.

Several broad classes of magnetic fluids are known in the art, however presently use of each suffers limitations in its applicability. For example, surfactants can be used in a bilayer to form aqueous magnetic fluids, however, the fluids tend to destabilize on dilution, due to desorption of the outer surfactant layer, and methods to circumvent this have not been too successful, and moreover, are not easily amenable to scale up. Another class of magnetic fluids is that of single-polymer-coated magnetic fluids. These particles, however, are either too small for easy capture or are not stable in high ionic strength environments. Magnetic nanoparticles embedded in a polymer matrix, have also been used similarly, however, these particles are typically much larger and are not colloidally stable, requiring agitation to remain suspended, and possess a relatively low surface area.

An improved technology, without these limitations, and providing inexpensive, large-scale production of magnetic fluids would have broad application, yet at present, is lacking in the art.

SUMMARY OF THE INVENTION

The invention provides, in one embodiment, a multi-polymer-coated magnetic nanocluster, comprising:
(a) super paramagnetic core particles;
(b) a first polymer attached thereto, comprising a chelating group, wherein attachment of said first polymer to said super paramagnetic core particles produces a first polymer-super paramagnetic core particle complex which is not colloidally stable, and clustering of said super paramagnetic core particles; and
(c) a second polymer attached thereto, wherein attachment of said second polymer stabilizes said multi-polymer-coated magnetic nanocluster.

In one embodiment, the super paramagnetic core particles comprise magnetite. In another embodiment, the chelating group is an iron-chelating group, which is, in another embodiment, a free carboxylic acid.

In another embodiment, the nanocluster ranges in size from 25-200 nm. In another embodiment, the nanocluster size is a function of the ratio of the chelating groups in the first polymer to iron atoms in the magnetite core particles. In one embodiment, the ratio is between 0.1 and 0.6. In another embodiment, nanocluster size is controlled via limiting the amount of polymer 1.

In another embodiment, the first polymer comprises acrylic acid, styrene sulfonic acid, vinyl sulfonic acid, vinyl benzyl trimethyl ammonium chloride, acrylamidopropyl trimethyl ammonium chloride, PEO, PPO or PAA, or any combination thereof. In another embodiment, the first polymer comprises acrylic acid, styrene sulfonic acid and vinyl sulfonic acid. According to this aspect, and in one embodiment, the concentration of vinyl sulfonic acid ranges from 25-50%, or in another embodiment, the concentration of styrene sulfonic acid ranges from 25-75%, or in another embodiment, the concentration of acrylic acid is roughly 25%. In another embodiment, the ratio of acrylic acid concentration to iron atom concentration ranges from 0.1-0.6, or in another embodiment, is 0.2.

In another embodiment, the first polymer comprises vinyl benzyl trimethyl ammonium chloride or acrylamidopropyl trimethyl ammonium chloride and acrylic acid. According to this aspect, and in one embodiment, the concentration of vinyl benzyl trimethyl ammonium chloride or acrylamidopropyl trimethyl ammonium chloride ranges from 25-90%, or in another embodiment, from 70-80%, or in another embodiment, is roughly 75%. In one embodiment, the ratio of acrylic acid concentration to iron atom concentration ranges from 0.1-0.6, or in another embodiment, is 0.2.

In another embodiment, the first polymer is a copolymer, comprising polyethylene oxide and polypropylene oxide grafted on polyacrylic acid. According to this aspect, and in one embodiment, the polyethylene oxide is grafted at a concentration of 8-16%. In another embodiment, the polypropylene oxide is grafted at a concentration of 0-8%. In another embodiment, the polyacrylic acid has a molecular weight of 5000. In another embodiment, the polymer concentration is 0.25-1.25 grams, or in another embodiment, 0.25 grams of polymer per gram of magnetite.

In another embodiment, the second polymer comprises acrylic acid, vinyl sulfonic acid, vinyl benzyl trimethyl ammonium chloride, acrylamidopropyl trimethyl ammonium chloride, polyethylene oxide, polypropylene oxide or polyacrylic acid, or any combination thereof. In another embodiment, the second polymer comprises poly acrylic acid, which in another embodiment, has a molecular weight of 2,000-250,000, or in another embodiment, 5,000. In one embodiment, the polymer concentration ranges from 0.1-0.5 grams of polymer per gram of magnetite, or in another embodiment, is 0.3 grams of polymer per gram of magnetite.

In another embodiment, the second polymer comprises a copolymer of acrylic acid and vinyl sulfonic acid. In one embodiment, according to this aspect, the concentration of acrylic acid and vinyl sulfonic acid ranges from 25-50%, or in another embodiment, is roughly 25%. In another embodiment, the polymer concentration ranges from 0.1-0.5 grams, or in another embodiment, is 0.4 grams of polymer per gram of magnetite.

In another embodiment, the second polymer stabilizes the multi-polymer-coated magnetic nanocluster by creating a steric shell around said core particles, or in another embodiment, by providing a charge to said multi-polymer-coated magnetic nanocluster. In another embodiment, the multi-polymer-coated magnetic nanocluster is stable in solutions of high ionic strength.

In another embodiment, the first polymer comprises styrene sulfonic acid, vinyl sulfonic acid and acrylic acid, and said second polymer comprises polyethylene oxide and polypropylene oxide grafted on polyacrylic acid, or polyacrylic acid, or acrylic acid and vinyl sulfonic acid. In another embodiment, the first polymer comprises vinyl benzyl trimethyl ammonium chloride or acrylamidopropyl trimethyl ammonium chloride and acrylic acid, and said second polymer comprises vinyl benzyl trimethyl ammonium chloride or acrylamidopropyl trimethyl ammonium chloride and acrylic acid. In another embodiment, the first polymer comprises polyethylene oxide and polypropylene oxide grafted on polyacrylic acid, and said second polymer comprises polyethylene oxide and polypropylene oxide grafted on polyacrylic acid, or polyacrylic acid, or acrylic acid and vinyl sulfonic acid.

In another embodiment, the multi-polymer-coated magnetic nanocluster further comprises a targeting moiety, which, in another embodiment, is an antibody, an antibody fragment, a receptor, Protein A, Protein G, biotin, avidin, streptavidin, a metal ion chelate, an enzyme cofactor, a nucleic acid or a ligand.

In another embodiment, this invention provides a solution comprising a multi-polymer-coated magnetic nanocluster, which is, in another embodiment, an aqueous solution, or in another embodiment, is one of high ionic strength.

In another embodiment, this invention provides a process for producing multi-polymer-coated magnetic nanoclusters, comprising the steps of:
(a) Contacting in an aqueous solution super paramagnetic core particles with a first polymer comprising a chelator, whereby first polymer attachment to said super paramagnetic core particles produces an instability in the first polymer-super paramagnetic core particle complex, and clustering of said super paramagnetic core particles; and
(b) Contacting the solution in (a) with a second polymer, whereby said second polymer stabilizes said polymer-magnetite particle complex forming multi-polymer-coated magnetic nanoclusters.

In one embodiment, the solution of multi-polymer-coated magnetic nanoclusters is further concentrated, which comprises, in another embodiment, precipitating the multi-polymer-coated magnetic nanoclusters. In another embodiment, the process for producing multi-polymer-coated magnetic nanoclusters further comprises the step of conjugating a targeting moiety to the multi-polymer-coated magnetic nanoclusters.

In another embodiment, this invention provides a method of separation comprising the steps of:
(i) Contacting a solution comprising a substance of interest with a multi-polymer-coated magnetic nanocluster of this invention, wherein said multi-polymer-coated magnetic nanocluster has an enhanced interaction with said substance of interest;
(ii) Providing conditions whereby said multi-polymer-coated magnetic nanocluster interacts with said substance of interest, forming a multi-polymer-coated magnetic nanocluster-substance of interest complex; and
(iii) Magnetically separating said multi-polymer-coated magnetic nanocluster-substance of interest complex from other components of said solution.

In one embodiment, the method is utilized to separate a biological substance of interest from a sample in solution. In one embodiment, the sample is a biological sample, which in one embodiment is a tissue homogenate, a cell lysate, a broth, or a cell or tissue culture.

In one embodiment, the biological substance is a eucaryotic cell, procaryotic cell, subcellular organelle, virus, protein, nucleic acid, carbohydrate, ligand, lipid or any combination thereof.

In another embodiment, the magnetic separation of the complex is via high gradient magnetic separation. In one embodiment, the method is utilized to separate a protein expressed by a cell from said cell. According to this aspect, and in one embodiment, the protein is strongly cationic.

In another embodiment, the method of this invention is conducted in a solution or broth. In another embodiment, the cell is a bacteria or yeast, and in another embodiment, the yeast is a *Pichia* species.

In another embodiment, this invention provides a method of separation comprising the steps of:
(a) Contacting a solution comprising a substance of interest with a multi-polymer-coated magnetic nanocluster of this invention, wherein said multi-polymer-coated magnetic nanocluster further comprises a targeting moiety;
(b) Providing conditions whereby said targeting moiety interacts with said substance of interest, forming a multi-polymer-coated magnetic nanocluster-substance of interest complex; and
(c) Magnetically separating said multi-polymer-coated magnetic nanocluster-substance of interest complex from other components of said biological sample.

In one embodiment, according to this aspect, the targeting moiety is an antibody, an antibody fragment, a receptor, Protein A, Protein G, biotin, avidin, streptavidin, a metal ion chelate, an enzyme cofactor, a nucleic acid, a ligand or a lectin. In another embodiment, the method is utilized to separate a biological substance of interest from a sample, which in one embodiment, is a biological sample, which in another embodiment, is a tissue homogenate, a cell lysate or a cell or tissue culture.

In another embodiment, the biological substance according to this aspect is a eucaryotic cell, procaryotic cell, subcellular organelle, virus, protein, nucleic acid, carbohydrate, ligand, lipid or any combination thereof.

In another embodiment, magnetic separation of the complex is via HGMS.

In another embodiment, this invention provides a method of separating an expressed protein from a virus expressing said protein, the method comprising the steps of:
(i) lysing a cell comprising a virus expressing a protein of interest;
(ii) contacting the lysate obtained in (a) with a multi-polymer-coated magnetic nanocluster of this invention;

(iii) providing conditions whereby said multi-polymer-coated magnetic nanocluster interacts with said expressed protein, forming a multi-polymer-coated magnetic nanocluster-expressed protein complex, whereby said conditions may also result in the formation of a multi-polymer-coated magnetic nanocluster-virus complex;

(iv) magnetically separating from other components a complex comprising a multi-polymer-coated magnetic nanocluster, wherein said complex may comprise expressed protein, virus, or mixtures thereof, in said complex;

(v) Contacting said complex with a solution of high ionic strength; and (vi) Collecting said expressed protein, whereby said solution of high ionic strength results in enhanced binding affinity of said virus for said multi-polymer-coated magnetic nanocluster, reduced binding affinity of said expressed protein for said multi-polymer-coated magnetic nanocluster, or a combination thereof, and wherein said effects on binding affinity enable preferential collection of said expressed protein thereby being a method of separating a recombinantly expressed protein from a virus expressing said protein.

According to this aspect of the invention, and in one embodiment, magnetic separation of the complex is via high gradient magnetic separation. In one embodiment, the multi-polymer-coated magnetic nanocluster is at a range in size of from 20-1000 nm. In another embodiment, the solution of high ionic strength ranges in concentration of from 0.1-0.4M. In another embodiment, the concentration of multi-polymer-coated magnetic nanocluster in solution ranges from 0.05-0.3%.

In another embodiment, the method further comprises the step of contacting the complex with a solution at high pH. In one embodiment, the solution is of low ionic strength.

In another embodiment, the method further comprises the step of collecting the virus.

In another embodiment, the multi-polymer-coated magnetic nanocluster comprises a copolymer of vinylsulfonic acid and acrylic acid, or in another embodiment, the multi-polymer-coated magnetic nanocluster comprises PEO, or in another embodiment, the multi-polymer-coated magnetic nanocluster comprises a mixture thereof.

BRIEF DESCRIPTION OF THE DRAWINGS

FIG. 1 schematically depicts the process of multi-polymer-coated magnetic nanocluster synthesis. Iron ions are precipitated with a base in the presence of a polymer to form nanoclusters. A second polymer is added to stabilize the clusters.

FIG. 2 demonstrates the synthesis of an embodiment of polymer 1 and 2 (a and b), respectively. Monomers are free radical polymerized to form an anionic polymer that attaches to a super paramagnetic particle, in this case magnetite, with its carboxylic acid functionality. An embodiment of Polymer 3 synthesis is shown in 2*c*, where graft copolymers are synthesized by attaching amino-terminated PEO and PPO side chains to a PAA backbone via an amidation reaction. The majority of the COOH groups are left unreacted for subsequent attachment to the magnetite nanoparticles.

FIG. 3 demonstrates particle size control accomplished via limiting the amount of polymer 1. When the amount of polymer 1 is small enough, clusters are formed that are large enough (>50 nm) for efficient HGMS capture, as evidenced by plotting the particle diameter as a function of the molar ratio of carboxyl groups in polymer 1 to iron ions in the magnetite particles in solution.

FIG. 4 demonstrates that particle size control may be a function of molecular size of polymer 2. Plotting the particle size versus the molecular size of poly acrylic acid secondary polymer demonstrates the formation of aggregates varying in size. Minimal changes in particle size were seen with polymer 2 molecular weight that was less than 15 kDa, above which bridging occurs.

FIG. 5 demonstrates protein purification using HGMS for proteins adsorbed onto multi-polymer coated magnetic nanoparticles. (a) Binding isotherms (25° C. pH=7) for cytochrome-c on magnetic nanoclusters. Binding was performed at several ionic strengths, with NaCl added. (b) Maximum binding capacity for magnetic nanoclusters as a function of ionic strength. (c) Elution of bound protein by 0.5M NaCl. Nearly quantitative recovery of the protein is obtained with 0.5M NaCl. (d) Fractional capture of nanoclusters by HGMS as a function of particle size. Clusters of larger than about 40 nm are required for sufficient capture. (e) Percentage of magnetic nanoclusters that remain stable after one binding/capture/desorption cycle. The addition of a secondary polymer is required to provide sufficient stability for re-use.

FIG. 6 schematically depicts a process for recovery of proteins from unclarified fermentation broth. The magnetic nanoclusters are added directly to the fermentation broth, where desired proteins are adsorbed. The solution is then run through a high gradient magnetic separation (HGMS) device to capture the magnetic clusters along with the desired protein.

FIG. 7 demonstrates cell binding to nanoclusters in fermentation broth. (A) Graphic depiction of the binding of cells and drosomycin to magnetic nanoclusters in fermentation broth. At pH=3, nanoclusters bind much more strongly to cells than to drosomycin, making their use in unclarified broth impossible. Positively charged nanoclusters bind even more strongly to cells than negatively charged nanoclusters do. (B) Graphic depiction of the zeta potential of cells and nanoclusters in fermentation broth. Both nanoclusters and cells are overall negatively charged at all pH values tested for binding, indicating that binding is due to positively charged patches on the surface FIG. 8 demonstrates pH effects of cell binding to magnetic nanoclusters. (A) Graphic depiction of charge of proteins vs. pH. Based on the amino acid sequence, the charge for drosomycin and an average protein (with all amino acids composition equal to overall amino acid abundance in *E. coli* [Lehninger, A. L., Biochemistry. 2nd edition ed. 1975, New York: Worth Publishers]) are similar, and match well with the cell binding. (B) Binding of cells to magnetic nanoclusters (0.12 wt %) in fermentation broth as a function of pH. The nanoclusters bind to cells strongly at low pH and bind only weakly at higher pH, indicating that a protein on the surface is responsible for binding. After washing the cells with pH=10 three times to desorb all proteins from the surface, binding still occurs, indicating that the protein is part of the cell wall and not drosomycin adsorbed on the surface. (C) Cells bound to magnetic nanoclusters as a function of pH with other, high pI proteins added. When lysozyme or cytochrome-c is added, cell binding is essentially unchanged, even though at pH>6 the magnetic nanoclusters reversibly flocculate with lysozyme added but do not without lysozyme, indicating that the binding is not physical entrapment in the flocs, and that adsorbed proteins are not responsible for cell binding.

FIG. 9 schematically depicts a model of the interaction energy between a nanoclusters and a yeast cell with a protein on the surface. All are assumed to be spheres, with the protein half out of the yeast surface, and thus closer to the particle than the yeast cell. Due to the high ionic strength and the curvature of the nanoclusters, the overall interaction can be attractive, even if the yeast surface and the particle are of the same charge.

Figure 9:
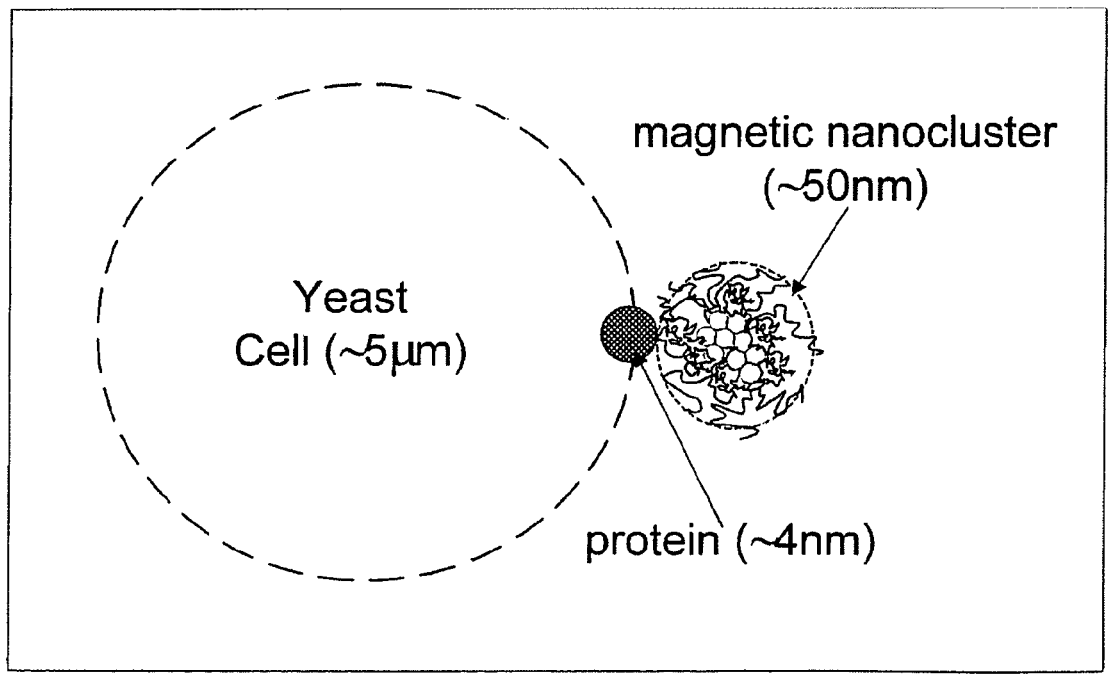
Figure 10:
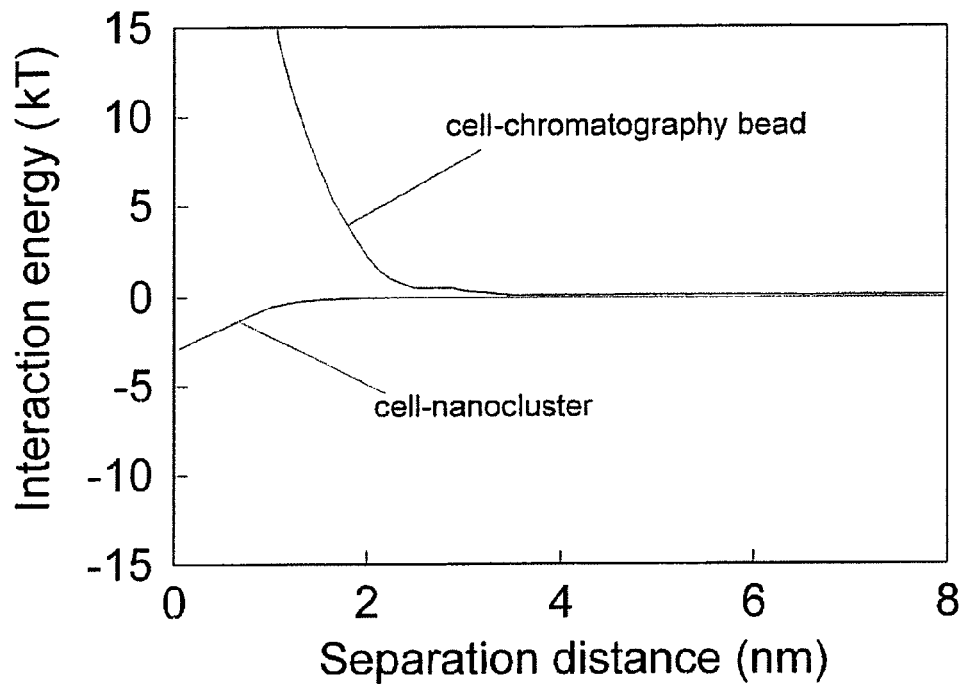

FIG. 10 graphically depicts the results of the model in FIG. 9 and Equation 6-1. For a 4 nm protein, 50 nm cluster and 5 mm cell at an ionic strength of 0.4, the cell nanoclusters interaction is attractive. When a 100 mm chromatography bead of the same charge is put in place of the nanoclusters the interaction is repulsive, due to the lower curvature of the bead and stronger interaction with the cell surface.

Figure 11:
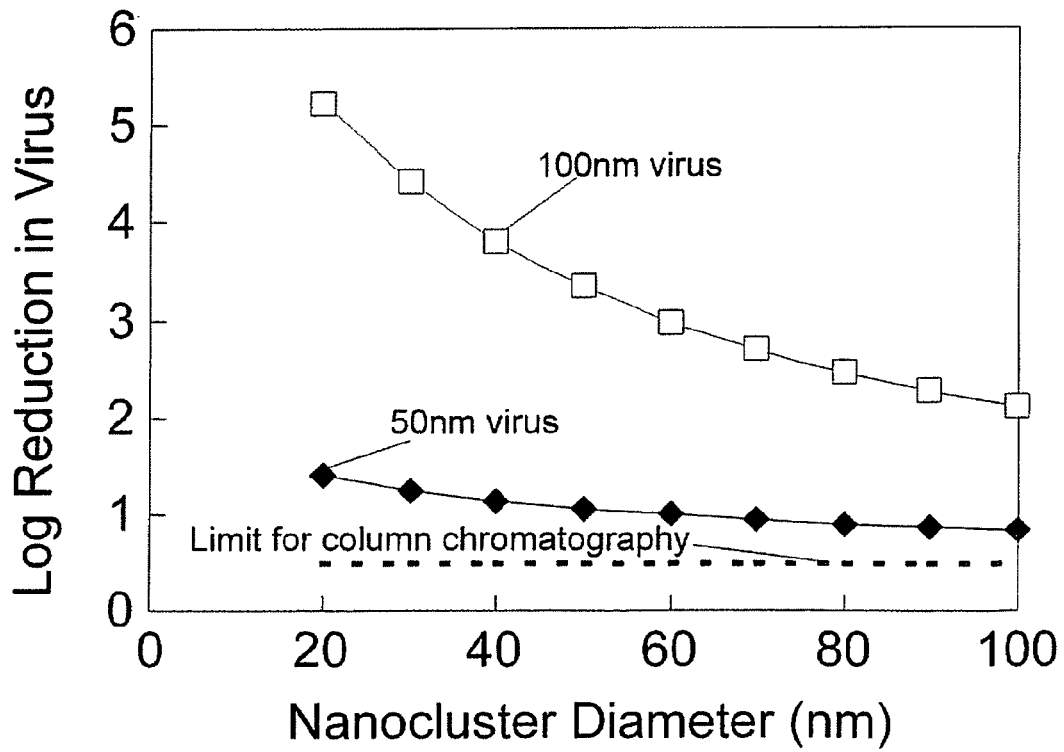

FIG. 11 graphically depicts the calculated log reduction in virus as a function of cluster size for 100 nm and 50 nm viruses. Smaller clusters have a higher affinity for the virus, due to a lower electrostatic repulsion with the viral surface.

Figures 12, 13:
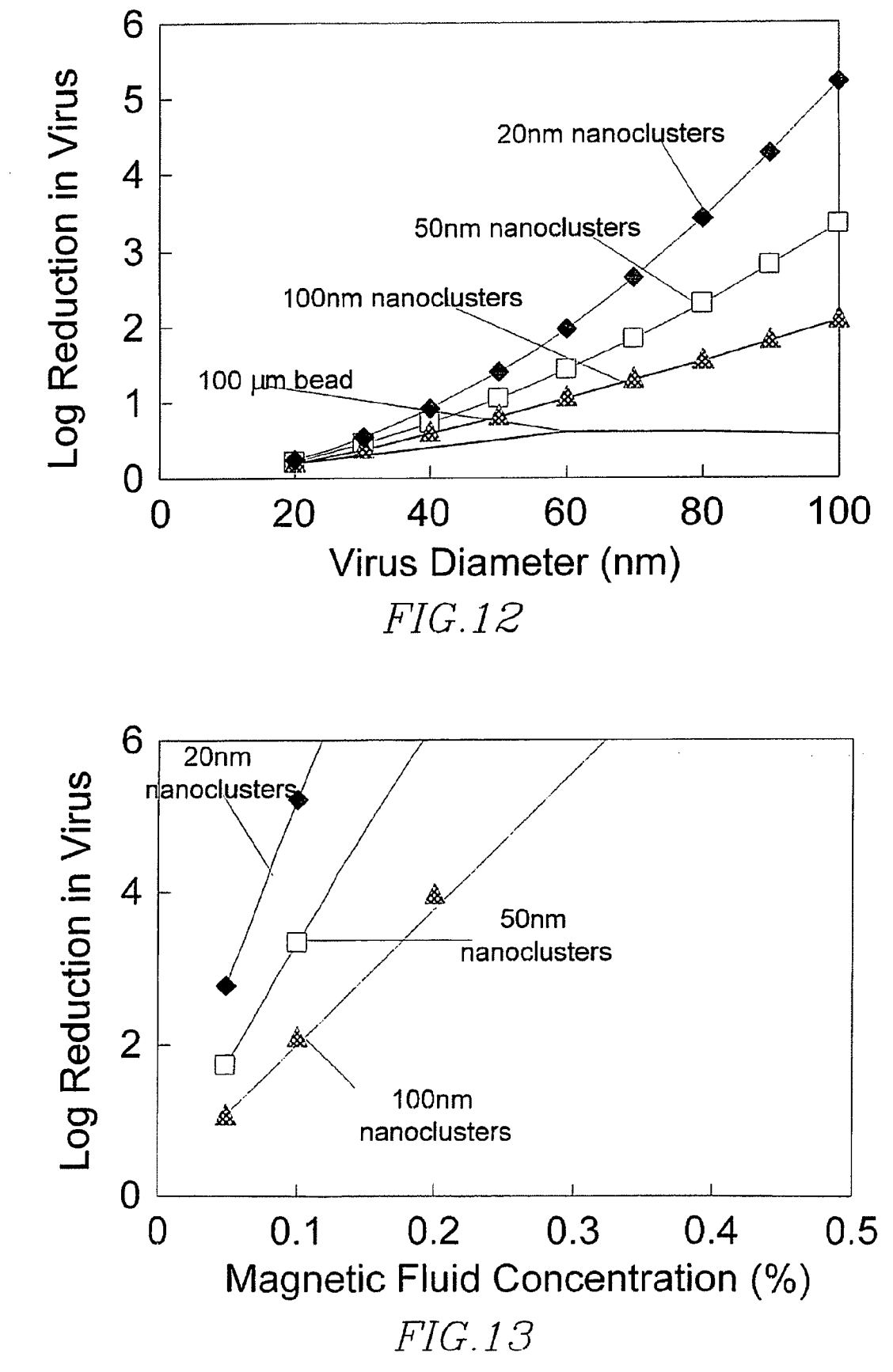

FIG. 12 graphically depicts the effect of virus size on log reduction. Larger viruses have more protein sites to be bound, and are thus more likely to have a nanocluster bound, while larger chromatography beads have a stronger electrostatic repulsion with larger viral particles and reach a maximum clearance at about 70 nm.

FIG. 13 graphically depicts the effect of magnetic nanocluster concentration on viral clearance, assuming that binding is in the linear regime. As the nanocluster concentration is increased, the fraction of virus bound increases.

FIG. 14 graphically depicts the effect of ionic strength on virus binding. As the ionic strength increases, protein binding affinity is reduced, but electrostatic repulsion is also reduced. Thus at higher ionic strength, most protein will not be bound, but most virus will, due to multipoint interactions. Washing of bound nanoparticles with high ionic strength buffer will elute bound protein while retaining viruses.

FIG. 15 demonstrates viral clearance as a function of protein surface density. When more protein is present on the surface, the fraction of viral particles bound increases.

FIG. 16 graphically depicts the effect of protein size on viral clearance. As the proteins on the surface become larger, the electrostatic repulsion is reduced, particularly for large particles. The total number of proteins on the surface also is reduced, which reduces the overall binding.

DETAILED DESCRIPTION OF THE INVENTION

This invention provides, in one embodiment, a multi-polymer-coated magnetic nanocluster, comprising super paramagnetic core particles, a first polymer attached thereto, comprising a chelating group, wherein attachment of said first polymer to said super paramagnetic core particles produces a first polymer-super paramagnetic core particle complex, which is not colloidally stable, and clustering of the super paramagnetic core particles, and a second polymer attached thereto, wherein attachment of said second polymer stabilizes said multi-polymer-coated magnetic nanocluster.

Multi-polymer-coated magnetic nanoclusters comprising a magnetite core were produced as exemplified hereinunder. According to this aspect of the invention, and in one embodiment, magnetic fluids consisting of 25-200 nm clusters of 8 nm magnetite ($Fe_3O_4$) cores coated with several different polymers were produced. It was found that the size of the magnetic nanoparticles can be tuned to a desired value, based on the characteristics of the polymer coating used. The clusters are colloidally stabilized via the application of a secondary polymer coating, whereas coating with a single polymer layer does not produce this effect. The tuning of particle size is useful, in one embodiment, for recovery of the multi-polymer-coated magnetic nanoparticles, since recovery is very difficult when the size is below 50 nm. In another embodiment, particle size tuning is useful in that the capacity of the particles for separations, as well as colloidal stability is enhanced dramatically as particle size is reduced.

In one embodiment, the multi-polymer-coated magnetic nanocluster are of a size that results in their remaining in solution for extended periods of time. In another embodiment, the nanocluster ranges in size from 20-1000 nm. In one embodiment, the nanocluster ranges in size from 25-200 nm. In one embodiment, the nanocluster ranges in size from 30-200 nm, or in another embodiment, the nanocluster ranges in size from 35-200 nm, or in another embodiment, the nanocluster ranges in size from 40-200 nm, or in another embodiment, the nanocluster ranges in size from 45-200 nm, or in another embodiment, the nanocluster ranges in size from 50-200 nm, or in another embodiment, the nanocluster ranges in size from 75-200 nm, or in another embodiment, the nanocluster ranges in size from 100-200 nm, or in another embodiment, the nanocluster ranges in size from 125-200 nm, or in another embodiment, the nanocluster ranges in size from 150-200 nm, or in another embodiment, the nanocluster ranges in size from 175-200 nm, or in another embodiment, the nanocluster ranges in size from 35-75 nm, or in another embodiment, the nanocluster ranges in size from 50-100 nm, or in another embodiment, the nanocluster ranges in size from 75-200 nm, or in another embodiment, the nanocluster ranges in size from 75-150 nm, or in another embodiment, the nanocluster ranges in size from 50-125 nm, or in another embodiment, the nanocluster ranges in size from 20-100 nm, or in another embodiment, the nanocluster ranges in size from 20-125 nm. In one embodiment, the nanocluster is 20 nm, or in another embodiment, the nanocluster is 40 nm, or in another embodiment, the nanocluster is 50 nm, or in another embodiment, the nanocluster is 60 nm, or in another embodiment, the nanocluster is 80 nm, or in another embodiment, 100 nm, in size.

In another embodiment, the nanocluster size is a function of the ratio of the chelating groups in the first polymer to iron atoms in the magnetite core particles. In one embodiment, the ratio is between 0.1 and 0.6. In another embodiment, the ratio ranges from 0.1 to 0.6, or in another embodiment, the ratio ranges from 0.1 to 0.3, or in another embodiment, the ratio ranges from 0.3 to 0.6, or in another embodiment, the ratio is 0.1, or in another embodiment, the ratio is 0.2, or in another embodiment, the ratio is 0.3, or in another embodiment, the ratio is 0.4, or in another embodiment, the ratio is 0.5, or in another embodiment, the ratio is 0.6. In another embodiment, nanocluster size is controlled via limiting the amount of polymer 1. In another embodiment, the nanocluster size is controlled via the molecular size of polymer 2.

Multi-polymer-coated magnetic nanoclusters of this invention comprise at least 2 polymers, which are attached to the super paramagnetic core particles, which when formed, are colloidally stable. In one embodiment, the attachment is a strong or weak interaction between the super paramagnetic core particles and the polymer(s).

In one embodiment, the super paramagnetic core particles comprise magnetite, which in one embodiment, refers to an iron ore that is strongly attracted by a magnet. In one embodiment it has a general formula of $Fe_3O_4$, which in another embodiment, possesses a $Fe^{2+}$ to $Fe^{3+}$ ratio of about 1:1.5 to about 1:2.5, or in another embodiment, about 1:2. In another embodiment, the super paramagnetic particles may comprise chemical equivalents thereof, such as $(Fe,M)OFe_20_3$ where M may be, in one embodiment, Zn, Co, Ni, Mn, or Cr. In another embodiment, the Fe 2+ to Fe 3+ ratio includes any ratio that permits the formation of superparamagnetic nanoparticles in accordance with the method of the present invention.

In another embodiment, the super paramagnetic core particles comprise a chelating group. In one embodiment, the chelating group is an iron-chelating group, which is, in another embodiment, a free carboxylic acid. In another embodiment, the super paramagnetic core particles comprise gamma or alpha iron oxide, chromium dioxide, ferrites, or various elements of metallic alloys.

In one embodiment, the polymer-coated magnetic nanoclusters comprise paramagnetic substances, which in one embodiment, refers to a substance that when placed in a magnetic field are magnetized parallel to the line of force in the field and proportional to the intensity of the field. In one embodiment, the polymer-coated magnetic nanoclusters comprise a super paramagnetic core to which the polymers of this invention are attached. In one embodiment, the term "superparamagnetic" refers to a class of substances that have a similar magnetism as ferromagnetic materials in the external magnetic field, but does not have a remnant magnetization after removal of the external magnetization field.

Multiple polymer coating of the superparamagnetic core particles is an element of this invention. In one embodiment, the polymers of this invention may be copolymers. In another embodiment, the polymers of this invention may be homo- or, in another embodiment heteropolymers. In another embodiment, the polymers of this invention are synthetic, or, in another embodiment, the polymers are natural polymers. In another embodiment, the polymers of this invention are free radical random copolymers, or, in another embodiment, graft copolymers. In one embodiment, the polymers may comprise proteins, peptides or nucleic acids. It is to be understood that any polymers which have affinity for super paramagnetic core particles, which when added sequentially produce a multi-polymer-coated magnetic nanocluster of this invention, are to be considered as part of this invention.

In one embodiment, the choice of polymer utilized may be a function of the charge of the magnetic particle employed. In one embodiment, the first polymer may comprise a random copolymer of acrylic acid, styrene sulfonic acid and vinyl sulfonic acid for negatively charged particles, a random copolymer of acrylic acid, vinylbenzyl trimethyl ammonium chloride and acrylamidopropyl trimethyl ammonium chloride for positively charged particles, and a graft copolymer with a backbone of acrylic acid and side chains of polyethylene oxide and polypropylene oxide. In one embodiment, the selection of polymer is in order to provide a hydrophobic domain and a hydophillic stabilizing shell for hydrophobic stabilization.

In another embodiment, the first polymer comprises acrylic acid, styrene sulfonic acid, vinyl sulfonic acid, vinyl benzyl trimethyl ammonium chloride, acrylamidopropyl trimethyl ammonium chloride, polyethylene oxide (PEO), polypropylene oxide (PPO) or polyacrylic acid (PAA), or a combination thereof. In another embodiment, the first polymer comprises acrylic acid, styrene sulfonic acid and vinyl sulfonic acid. According to this aspect, and in one embodiment, the concentration of vinyl sulfonic acid ranges from 25-50%, or in another embodiment, the concentration of styrene sulfonic acid ranges from 25-75%, or in another embodiment, the concentration of acrylic acid is roughly 25%. In another embodiment, the ratio of acrylic acid concentration to iron atom concentration ranges from 0.1-0.6, or in another embodiment, is 0.2.

In another embodiment, the first polymer comprises 25% acrylic acid, 50% vinyl sulfonic acid, 25% styrene sulfonic acid. According to this aspect of the invention, and in another embodiment, the molecular weight of the resulting polymer 1 may be 3, 5, 9, 12, 17, 32 or 70 kDa, or a range thereof. In another embodiment, the first polymer comprises 25% acrylic acid, 25% vinyl sulfonic acid, 50% styrene sulfonic acid. According to this aspect of the invention, and in another embodiment, the molecular weight of the resulting polymer 1 may be 2, 4, 5, 7, 10, 19 or 38 kDa, or a range thereof. In another embodiment, the first polymer comprises 25% acrylic acid, 75% styrene sulfonic acid. According to this aspect of the invention, and in another embodiment, the molecular weight of the resulting polymer 1 may be 3, 5, 12, 16, 23, 44, 102, 210 or 300 kDa, or a range thereof. In another embodiment, the first polymer comprises 20% acrylic acid, 80% vinyl sulfonic acid, or in another embodiment, 30% acrylic acid, 70% vinyl sulfonic acid, or in another embodiment, 40% acrylic acid, or in another embodiment, 60% vinyl sulfonic acid. According to this aspect of the invention, and in another embodiment, the molecular weight of the resulting polymer 1 may be 1, 2, 3, 4, 5, 6, 7 or 11 kDa. In another embodiment, the first polymer comprises 25% acrylic acid, 75% acrylamidopropyltrimethyl ammoniumchloride. According to this aspect of the invention, and in another embodiment, the molecular weight of the resulting polymer 1 may be 2, 3, 5, 10, 19, 35 or 260 kDa. In another embodiment, the first polymer comprises 25% acrylic acid, 75% vinylbenzyl trimethyl ammonium chloride. According to this aspect of the invention, and in another embodiment, the molecular weight of the resulting polymer 1 may be 11, 16, 36 or 170 kDa.

In another embodiment, the first polymer comprises vinyl benzyl trimethyl ammonium chloride or acrylamidopropyl trimethyl ammonium chloride and acrylic acid. According to this aspect, and in one embodiment, the concentration of vinyl benzyl trimethyl ammonium chloride or acrylamidopropyl trimethyl ammonium chloride ranges from 25-90%, or in another embodiment, from 70-80%, or in another embodiment, is roughly 75%. In one embodiment, the ratio of acrylic acid concentration to iron atom concentration ranges from 0.1-0.6, or in another embodiment, is 0.2.

In another embodiment, the first polymer is a copolymer, comprising PEO and PPO grafted on PAA. According to this aspect, and in one embodiment, the PEO is grafted at a concentration of 8-16%. In another embodiment, the PPO is grafted at a concentration of 0-8%. In another embodiment, the PAA has a molecular weight of 5000. In another embodiment, the polymer concentration is 0.25-1.25 grams, or in another embodiment, 0.25 grams of polymer per gram of magnetite.

In another embodiment, the polymer molecular weight of polymer 1 may be varied. In one embodiment, the molecular weight of the first polymer may range from 1-300, 1-5, 1-10, 10-20, 20-25, 1-25, 20-30, 30-40, 40-50, 25-50, 50-70, 70-100, 50-100, 100-150, 150-170, 170-200, 150-200, 100-200, 200-250, 250-300, 100-300, or 200-300 kDa.

In another embodiment, the coating of the super-paramagnetic particles with polymer 1 may be enhanced by heating the reaction solution. Temperatures from about 45-50° C. to temperatures as high as 90° C. were demonstrated herein to facilitate polymer coating of the super paramagnetic core particles. In one embodiment, a temperature of 80° C., or in another embodiment, a temperature of 85° C., or in another embodiment, a temperature of 75° C., or in another embodiment, a temperature of 70° C., or in another embodiment, a temperature of 65° C., or in another embodiment, a temperature of 60° C. is maintained for polymer coating of the super paramagnetic core particles via the methods of this invention.

Attachment of the second polymer provides for colloidal stabilization of the formed multi-polymer coated magnetic nanoclusters of this invention. In one embodiment, the term "stabilized" or "stabilization" refers to the stability of the resulting nanoclusters in solution following their production. In one embodiment, the terms "stabilized", "stabilization" or "colloidally stable", or "colloidal stabilization" refer to the fact that the multi-polymer coated magnetic nanoclusters do not aggregate or "settle out" in solution. In another embodiment, the multi-polymer coated magnetic nanoclusters do not change in their chemical composition over a particular period of time.

In one embodiment, the multi-polymer coated magnetic nanoclusters form a colloid, which, in one embodiment, refers to the homogeneous, non-crystalline nature of the nanoclusters dispersed in solution, wherein the nanoclusters, in one embodiment, do not settle, and in another embodiment, cannot be separated by ordinary filtration or centrifugation.

In one embodiment, the second polymer comprises acrylic acid, vinyl sulfonic acid, vinyl benzyl trimethyl ammonium chloride, acrylamidopropyl trimethyl ammonium chloride, polyethylene oxide, polypropylene oxide or polyacrylic acid, or any combination thereof.

In another embodiment, the second polymer comprises poly acrylic acid, which in another embodiment, has a molecular weight of 2-250 kDa. In another embodiment, the molecular weight of the polyacrylic acid used as the second polymer is 2, 5, 8, 15, 30, 50, 70, 100 or 250 kDa. In one embodiment, the polymer concentration ranges from 0.1-0.5 grams of polymer per gram of magnetite, or in another embodiment, is 0.3 grams of polymer per gram of magnetite.

In another embodiment, the second polymer comprises a copolymer of acrylic acid and vinyl sulfonic acid. In one embodiment, according to this aspect, the concentration of acrylic acid and vinyl sulfonic acid ranges from 25-50%, or in another embodiment, is roughly 25%. In another embodiment, the molecular weight of the second polymer according to this aspect may be 10 kDa.

In another embodiment, the second polymer comprises vinyl benzyl trimethyl ammonium chloride and acrylic acid. In another embodiment, the second polymer comprises acrylamidopropyl trimethyl ammonium chloride and acrylic acid. According to this aspect, and in one embodiment, the acrylic acid may be at a concentration of 25%, and the acrylamidopropyl trimethyl ammonium chloride at a concentration of 75%, with the polymer molecular weight being roughly 10 kDa.

In another embodiment, the second polymer comprises PEO and/or PPO grafted on PAA. In one embodiment, according to this aspect of the invention, the second polymer comprises a poly (acrylic acid) backbone of 5 kDa in size, with 16% grafting of poly(ethylene oxide), 3 kDa in size. In another embodiment, the second polymer comprises a poly (acrylic acid) backbone of 5 kDa in size, with 8% grafting of poly(ethylene oxide), 3 kDa in size and 8% grafting of poly (propylene oxide), 2 kDa in size.

In another embodiment, the polymer concentration ranges from 0.1-0.5 grams, or in another embodiment, is 0.4 grams of polymer per gram of magnetite.

In another embodiment, the second polymer stabilizes the multi-polymer-coated magnetic nanocluster by creating a steric shell around the core particles, or in another embodiment, by providing a charge to the multi-polymer-coated magnetic nanocluster. In another embodiment, the multi-polymer-coated magnetic nanocluster is stable in solutions of high ionic strength.

In another embodiment, the multi-polymer-coated magnetic nanocluster comprises a first polymer comprising styrene sulfonic acid, vinyl sulfonic acid and acrylic acid, and a second polymer comprising PEO and PPO grafted on PAA, or PAA, or acrylic acid and vinyl sulfonic acid. In another embodiment, the first polymer comprises vinyl benzyl trimethyl ammonium chloride or acrylamidopropyl trimethyl ammonium chloride and acrylic acid, and the second polymer comprises vinyl benzyl trimethyl ammonium chloride and acrylic acid or acrylamidopropyl trimethyl ammonium chloride and acrylic acid.

In another embodiment, the first polymer comprises PEO and PPO grafted on PAA, and said second polymer comprises PEO and PPO grafted on PAA, or PAA, or acrylic acid and vinyl sulfonic acid.

It is to be understood that an extremely large number of combinations of polymers may be utilized to form the multi-polymer-coated magnetic nanoclusters of this invention, with those listed hereinabove serving as a small representation of the possible combinations. Each of the possible combinations is to be considered, however, as an embodiment of this invention.

In another embodiment, the multi-polymer-coated magnetic nanocluster further comprises a targeting moiety. The term "targeting moiety", in one embodiment, refers to a specificity conferred to the moiety, which results in attachment of the moiety to a cognate partner, or, in another embodiment, an ability to specifically "target" the moiety to a desired cognate partner molecule. The targeting moiety may, in one embodiment, facilitate attachment of the multi-polymer-coated magnetic nanocluster, through the targeting moiety, to a protein or glycoprotein of interest, in one embodiment, or, in another embodiment, to a nucleic acid of interest, or in another embodiment, to a cellular fraction of interest.

In one embodiment, the targeting moiety enhances attachment to a molecule in low abundance, which is of interest. In another embodiment, the targeting moiety enhances attachment following supply of an energy source, such as a UV light source. In one embodiment, the targeting moiety is chemically attached to the polymers via a chemical cross-linking group, or in another embodiment, forms a stable association with a polymer of the multi-polymer-coated magnetic nanocluster, or, in another embodiment, forms an association with the a polymer of the multi-polymer-coated magnetic nanocluster, which readily dissociates following changes in solution conditions, such as, for example, salt concentration or pH.

In one embodiment, the targeting moiety may be an antibody, which specifically recognizes a molecule of interest, such as a protein or nucleic acid. In another embodiment, the antibody may specifically recognize a reporter molecule attached to a molecule of interest. In another embodiment, the targeting moiety may be an antibody fragment, Protein A, Protein G, biotin, avidin, streptavidin, a metal ion chelate, an enzyme cofactor, or a nucleic acid. In another embodiment, the targeting moiety may be a receptor, which binds to a cognate ligand of interest, or associated with a cell or molecule of interest, or in another embodiment, the targeting moiety may be a ligand which is used to "fish out" a cell via interaction with its cognate receptor.

It is to be understood that any component of interest, such as a cell, or component thereof, wherein its separation from other materials is desired, which is amenable to the present technology is to be considered as part of this invention.

For example, in one embodiment, the multi-polymer-coated magnetic nanoclusters may be used to separate or remove a desired substance from other substances, such as to tag and remove cancerous or other cells or substances from a biological environment be it in vitro or in vivo.

In one embodiment, use of the multi-polymer-coated magnetic nanoclusters for cell separations may be accomplished, as follows: a mixed population of cells obtained from various body fluids, such as bone marrow, blood, urine, sputum or secretion is obtained, using standard procedures. The multi-polymer-coated magnetic nanoclusters may be directly labelled, with specific antibodies to receptors expressed on the cell surface of the cell of interest. After binding of the labeled multi-polymer-coated magnetic nanoclusters to the target cells of interest is allowed to occur, magnetic separation of the magnetic particles from the suspension is performed. A similar scheme may be employed for a protein of interest, or nucleic acid of interest, for isolation from a biological sample, a culture medium, a bacterial or yeast culture, and many other scenarios, as will be apparent to one skilled in the art.

In one embodiment, the multi-polymer-coated magnetic nanoclusters are used for enrichment of particular cell populations, which differ in terms of their size, membrane charge, etc., which are present in a mixed population. In one embodiment, the population of interest shows greater binding affinity for the multi-polymer-coated magnetic nanoclusters of this invention, as compared to other cell populations and the population of interest is removed and dissociated from the nanoclusters. In another embodiment, the population or populations of interest exhibit less affinity for the multi-polymer-coated magnetic nanoclusters, as compared to non-desirable populations, whose removal is accomplished via contact with the multi-polymer-coated magnetic nanoclusters. It is to be understood that any use of multi-polymer-coated magnetic nanoclusters of this invention for the purpose of enriching cell populations or separations is to be considered as part of this invention.

In one embodiment, the multi-polymer-coated magnetic nanoclusters may be in a composition that is biocompatible, and in another embodiment, may be mixed with suitable pharmaceutically acceptable carriers or excipients, such as disclosed in Remington's Pharmaceutical Sciences, Mack Publishing Company, Easton, Pa., USA, 1985. The nanoparticles may be used in the treatment or diagnosis of certain conditions such as in tagging, detecting and/or removing cancer cells for example from a sample or tissue. In another embodiment, the multi-polymer-coated magnetic nanoclusters may also be utilized in the detoxification and/or valuable recovery of a desired substance, from domestic and industrial wastes.

In another embodiment, this invention provides a solution comprising a multi-polymer-coated magnetic nanocluster, which is, in another embodiment, an aqueous solution, or in another embodiment, is one of high ionic strength.

In one embodiment, the magnetic properties of the multi-polymer-coated magnetic nanocluster is such that it only exhibits magnetic behavior when in a magnetic field gradient, and does not become permanently magnetized.

In another embodiment, this invention provides a process for producing polymer-coated magnetic nanoclusters, comprising the steps of contacting in an aqueous solution, super paramagnetic core particles with a first polymer comprising a chelator, whereby attachment of said first polymer to said super paramagnetic core particles produces a first polymer-super paramagnetic core particle complex, which is not colloidally stable, and clustering of the super paramagnetic core particles, and contacting the solution comprising a first polymer-super paramagnetic core particle complex with a second polymer, whereby the second polymer stabilizes the polymer-magnetite particle complex, forming polymer-coated magnetic nanoclusters.

In one embodiment, the solution of polymer-coated magnetic nanoclusters is further concentrated, which comprises, in another embodiment, precipitating the polymer-coated magnetic nanoclusters. In one embodiment, precipitation may be accomplished with any number of appropriate solvents, such as acetone, methanol, ethanol, THF, acetonitrile, or any water-soluble organic solvent. In another embodiment, recovery of the polymer-coated magnetic nanoclusters following precipitation may be accomplished via magnetic decanting of the solution. In another embodiment, the polymer-coated magnetic nanoclusters may be suspended in an aqueous solution, and may be sonicated following resuspension.

As described further hereinabove, the process for producing polymer-coated magnetic nanoclusters may be further manipulated via the types of polymers used, their molecular size, limiting the amount of polymer 1 added, the size of polymer 2, or the temperature at which the process is conducted, or a combination thereof, each of which represents an embodiment of this invention.

In another embodiment, the process for producing polymer-coated magnetic nanoclusters further comprises the step of conjugating a targeting moiety to the polymer-coated magnetic nanoclusters, as described further hereinabove.

In another embodiment, this invention provides a method of separation comprising the steps of contacting a solution comprising a substance of interest with a multi-polymer-coated magnetic nanocluster of this invention, wherein the multi-polymer-coated magnetic nanocluster has an enhanced interaction with the substance of interest, providing conditions whereby the multi-polymer-coated magnetic nanocluster interacts with the substance of interest, forming a multi-polymer-coated magnetic nanocluster-substance of interest complex, and magnetically separating the multi-polymer-coated magnetic nanocluster-substance of interest complex from other components of said biological sample.

In one embodiment, the method is utilized to separate a biological substance of interest from a sample in solution. In one embodiment, the sample is a biological sample, which in one embodiment is a tissue homogenate, a cell lysate, a broth, a cell or tissue culture.

In one embodiment, the biological substance is a eucaryotic cell, procaryotic cell, subcellular organelle, virus, protein, nucleic acid, carbohydrate, ligand, lipid or any combination thereof.

In another embodiment, the magnetic separation of the complex is via high gradient magnetic separation. In one embodiment, the method is utilized to separate a protein expressed by a cell from said cell. According to this aspect, and in one embodiment, the protein is strongly cationic.

In another embodiment, the method of this invention is conducted in a solution or broth. In another embodiment, the cell is a bacteria or yeast, and in another embodiment, the yeast is a *Pichia* species.

According to this aspect of the invention, and in one embodiment, magnetic separation of the complex is via high gradient magnetic separation. In one embodiment, the multi-polymer-coated magnetic nanocluster is at a range in size of from 20-1000 nm. In another embodiment, the solution of high ionic strength ranges in concentration of from 0.1-0.4M. In another embodiment, the concentration of multi-polymer-coated magnetic nanocluster in solution ranges from 0.05-0.3%.

In another embodiment, this invention provides a method of separation comprising the steps of:
(i) Contacting a solution comprising a substance of interest with a multi-polymer-coated magnetic nanocluster of this invention, wherein said multi-polymer-coated magnetic nanocluster has an enhanced interaction with said substance of interest;
(ii) Providing conditions whereby said multi-polymer-coated magnetic nanocluster interacts with said substance of interest, forming a multi-polymer-coated magnetic nanocluster-substance of interest complex; and
(iii) Magnetically separating said multi-polymer-coated magnetic nanocluster-substance of interest complex from other components of said solution.

In one embodiment, the method is utilized to separate a substance of interest from a sample in solution. In one embodiment, the substance of interest is biological and the sample is a biological sample, which in one embodiment is a tissue homogenate, a cell lysate, a cell or tissue culture.

In one embodiment, the biological substance of interest is a eucaryotic cell, procaryotic cell, subcellular organelle, virus, protein, nucleic acid, carbohydrate, ligand, lipid or any combination thereof.

In another embodiment, the magnetic separation of the complex is via high gradient magnetic separation. In one embodiment, the method is utilized to separate a protein expressed by a cell from said cell. According to this aspect, and in one embodiment, the protein is strongly cationic.

In one embodiment, the cell is a bacteria or yeast. In one embodiment, it is desirable to separate prokaryotic or eukaryotic cells in a culture system or broth, or in another embodiment, it is desirable to isolate a protein expressed in a culture comprising prokaryotic or eukaryotic cells. In another embodiment, the prokaryotic or eukaryotic cells may be engineered to express a heterologous protein, which, in another embodiment, is desirable to separate from the bacteria or eukaryotic cells expressing the protein.

In another embodiment, the method of this invention is conducted in a solution or broth, which may, in another embodiment, be any such solution or broth, suitable for the particular substance being isolated, and the environment the substance is being isolated from, as will be appreciated by one skilled in the art.

For example, and in one embodiment, appropriate conditions for isolating proteins expressed by bacteria in culture or broth may be found in Sambrook et al., 1989, Molecular Cloning, A Laboratory Manual, (Volumes 1-3) Cold Spring Harbor Press, N.Y.; and Ausubel et al., 1989, or Current Protocols in Molecular Biology, Green Publishing Associates and Wiley Interscience, N.Y.

In another embodiment, the proteins of interest may be expressed in mammalian cells, which may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. In addition, any of the media described in Ham et al., Meth. Enz., 58: 44 [1979], Barnes et al., Anal. Biochem., 102: 255 [1980], U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the mammalian cells.

Any of the media or broth may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN.™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, will be apparent to the ordinarily skilled artisan (see, for example, Mammalian Cell Biotechnology: a Practical Approach, M. Butler, ed. (IRL Press, 1991).

In one embodiment, the protein being separated is secreted from the cell expressing the same. In another embodiment, the protein is expressed intracellularly.

In one embodiment, the cell expressing the protein, or in another embodiment, the cell comprising a virus which is genetically engineered to produce the protein is lysed, by means as will be known to one skilled in the art, such as, for example, via the use of detergent or osmotic shock.

In one embodiment, the protein is separated via the methods of this invention, as described. In another embodiment, the culture medium, or in another embodiment, cell lysate, or in another embodiment, tissue/organ homogenate is centrifuged to remove particulate cell debris, and the solution, lysate, homogenate, etc., is fractionated on an ion-exchange column, and/or in another embodiment, chromatography on silica or on a cation-exchange resin such as DEAE; and/or in another embodiment, gel filtration, following which, magnetic separation according to the methods of this invention are performed. In one embodiment, the protein is not particularly cationic, and the methods employed are in order to diminish contaminating virus present in the protein preparation.

In another embodiment, a protease inhibitor, such as phenyl methyl sulfonyl fluoride (PMSF) may be used in the methods of this invention, in order to inhibit proteolytic degradation during purification.

In another embodiment, the methods of this invention are utilized to isolate protein expressed in the yeast *Pichia*, as exemplified hereinbelow.

In another embodiment, this invention provides a method of separating an expressed protein from a virus expressing said protein, the method comprising the steps of:
(i) lysing a cell comprising a virus expressing a protein of interest;
(ii) contacting the lysate obtained in (a) with a multi-polymer-coated magnetic nanocluster of this invention;
(iii) providing conditions whereby said multi-polymer-coated magnetic nanocluster interacts with said expressed protein, forming a multi-polymer-coated magnetic nanocluster-expressed protein complex, whereby said conditions may also result in the formation of a multi-polymer-coated magnetic nanocluster-virus complex;
(iv) magnetically separating from other components a complex comprising a multi-polymer-coated magnetic nanocluster, wherein said complex may comprise expressed protein, virus, or mixtures thereof, in said complex;
(v) Contacting said complex with a solution of high ionic strength; and
(vi) Collecting said expressed protein, whereby said solution of high ionic strength results in enhanced binding affinity of said virus for said multi-polymer-coated magnetic nanocluster, reduced binding affinity of said expressed protein for said multi-polymer-coated magnetic nanocluster, or a combination thereof, and wherein said effects on binding affinity enable preferential collection of said expressed protein thereby being a method of separating a recombinantly expressed protein from a virus expressing said protein.

Figures 14, 15:
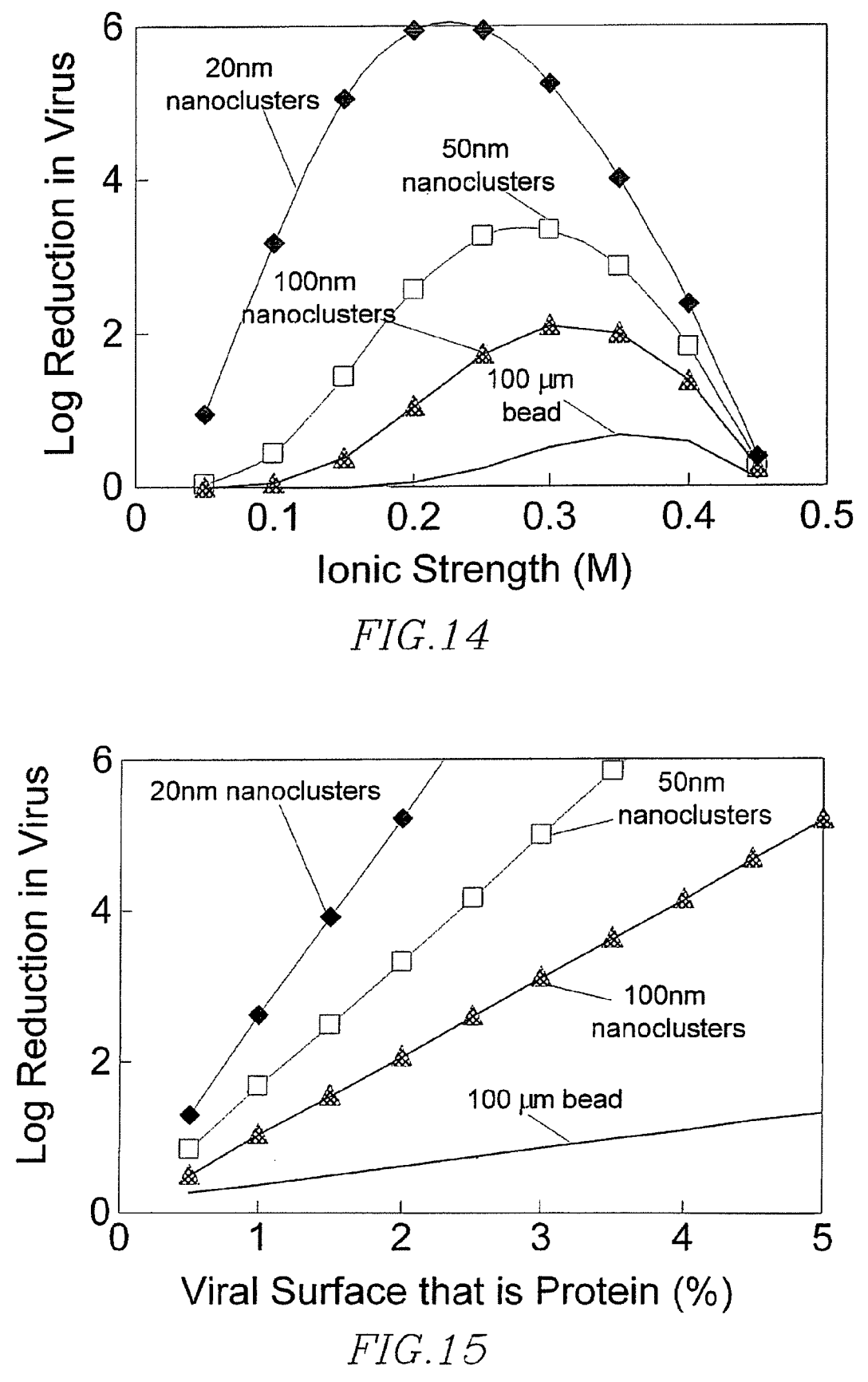

According to this aspect of the invention, and in one embodiment, free protein and viruses in solution, media or broth may be separated from each other via the methods of this invention. The present invention exemplifies one such embodiment (Example 8), where in a solution of 0.3M ionic strength, greater than 99.9% of 100 nm viruses are bound to 50 nm nanoclusters, as described, while less than 30% of the free protein is, due to multiple interactions with the nanocluster. Binding performed at 0.3M ionic strength result in a 3-log reduction of virus, while 70% of the protein is unbound. If the nanoclusters are eluted with 0.3M NaCl repeatedly, only 0.1% of the virus will be lost, but 70% of the protein will be recovered, and after several such elutions, nearly all the virus will be captured but nearly all the protein will be eluted (FIG. 14).

According to this aspect of the invention, and in one embodiment, a process for separation may comprise adding magnetic nanoclusters to a protein and virus mixture, passing the solution through HGMS, washing the column with a solution of high ionic strength (~0.3M NaCl) until the protein is no longer eluted, and eluting the nanoclusters with a high pH, low ionic strength solution to remove the virus.

It is to be understood that the multi-polymer-coated magnetic nanocluster may be used at a range in size as described hereinabove, and represents any embodiment herein disclosed.

In one embodiment, the cell expresses a protein, which is not encoded within the viral genome, and the method is utilized to separate the proteins from the cell, wherein the cell culture comprises a virus. In another embodiment, the protein is encoded within the viral genome, which utilizes the cellular machinery for protein expression.

In one embodiment, the solution of high ionic strength employed in the methods of this invention may range in concentration of from 1 mM-2M. In one embodiment, the solution of high ionic strength employed in the methods of this invention may range in concentration of from 0.05-0.6M. In one embodiment, the ionic strength employed may range in concentration of from 0.1M-0.3M, or in another embodiment, from 0.1M-0.4M, or in another embodiment, from 0.1M-0.5M, or in another embodiment, from 0.1M-0.25M.

In another embodiment, the concentration of multi-polymer-coated magnetic nanocluster in solution ranges from 0.0001-15%. In another embodiment, the concentration of multi-polymer-coated magnetic nanocluster in solution ranges from 0.05-0.3%. In one embodiment, the concentration of multi-polymer-coated magnetic nanocluster in solution ranges from 0.025-0.6%, or in another embodiment, the concentration of multi-polymer-coated magnetic nanocluster in solution ranges from 0.05-0.5%, or in another embodiment, the concentration of multi-polymer-coated magnetic nanocluster in solution ranges from 0.05-1%.

In another embodiment, according to this aspect of the invention, the multi-polymer-coated magnetic nanocluster comprises a copolymer of vinylsulfonic acid and acrylic acid, or in another embodiment, the multi-polymer-coated magnetic nanocluster comprises PEO, or in another embodiment, the multi-polymer-coated magnetic nanocluster comprises a mixture thereof.

In one embodiment, the methods of this invention are useful in removing viruses from a culture, which are too small to be removed by traditional filtration or centrifugation, obviating the need for ultrafiltration, which carries a large expense, or the need for viral inactivation by acids or detergents, which may affect protein activity.

In another embodiment, this invention provides a method of separation comprising the steps of contacting a solution comprising a substance of interest with a polymer-coated magnetic nanocluster of this invention, wherein said polymer-coated magnetic nanocluster further comprises a targeting moiety, providing conditions whereby the targeting moiety interacts with the substance of interest, and forming a polymer-coated magnetic nanocluster-substance of interest complex; and magnetically separating the polymer-coated magnetic nanocluster-substance of interest complex from other components of said biological sample.

In one embodiment, the targeting moiety is an antibody, a receptor, a ligand or a lectin.

In another embodiment, the separation methods of this invention are utilized to separate any biological substance of interest from a sample, as described hereinabove.

Figure 5A:
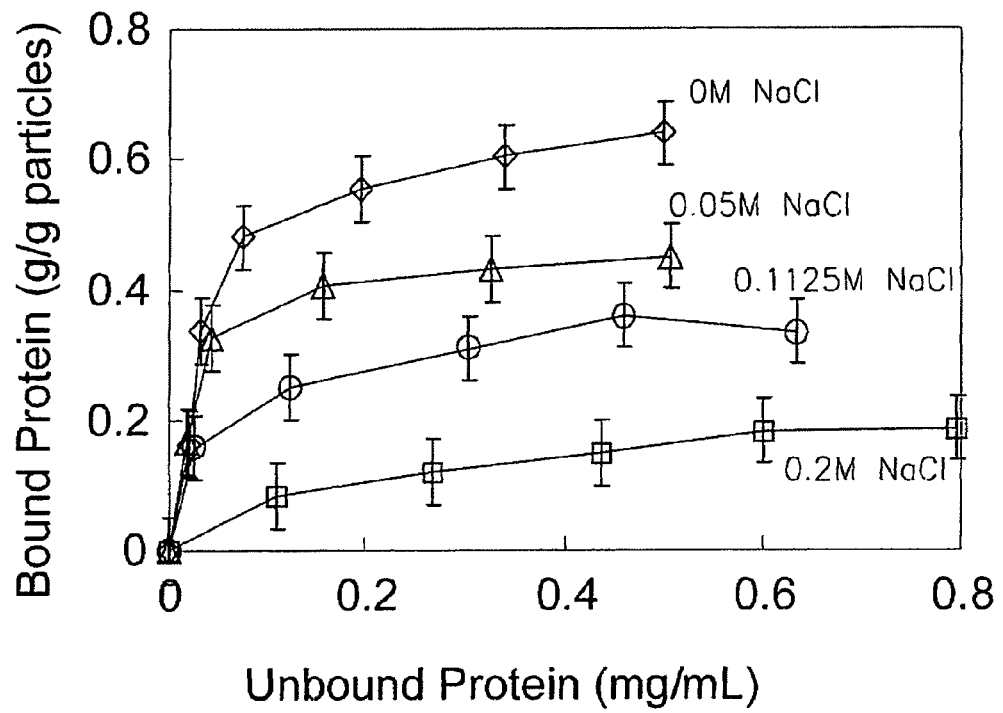
Figure 5B:
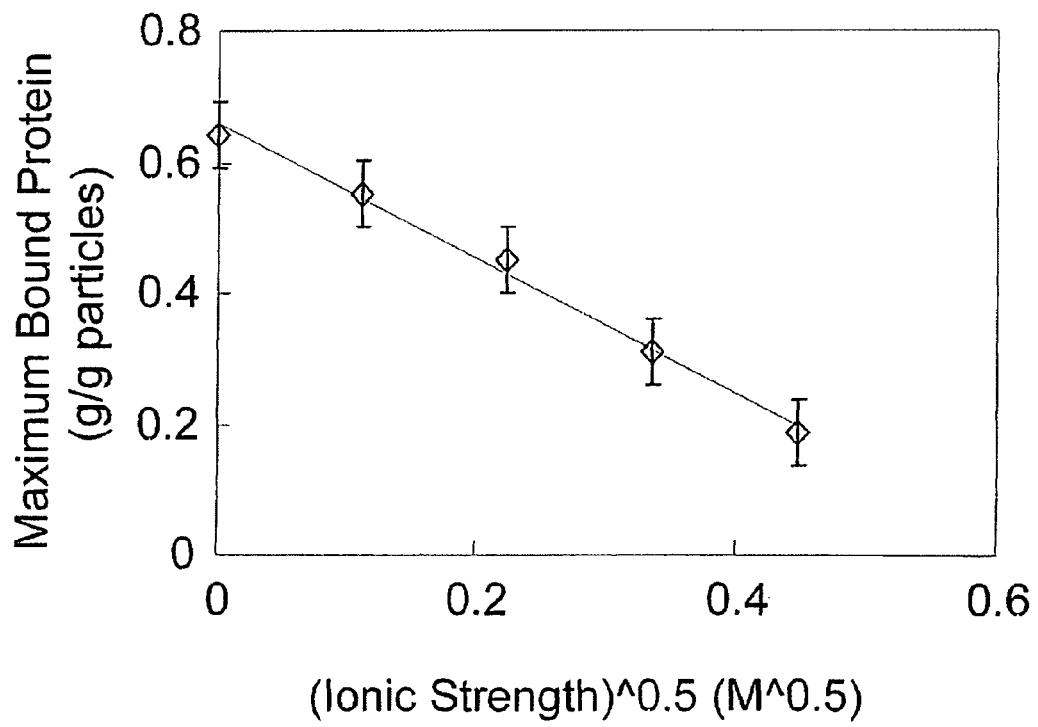
Figure 5C:
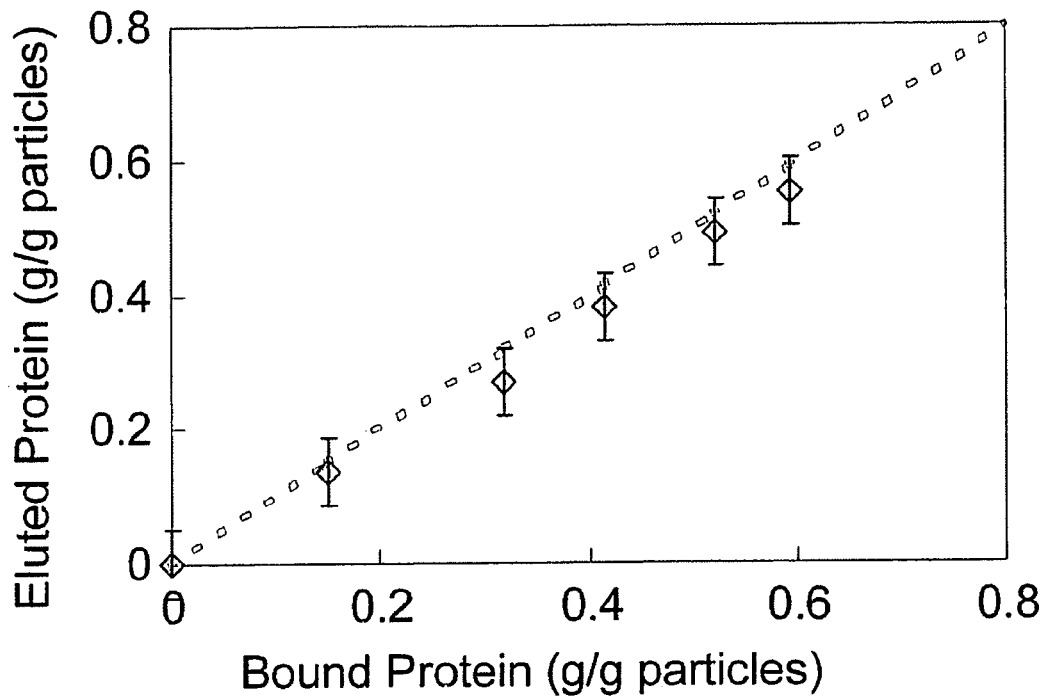
Figure 5D:
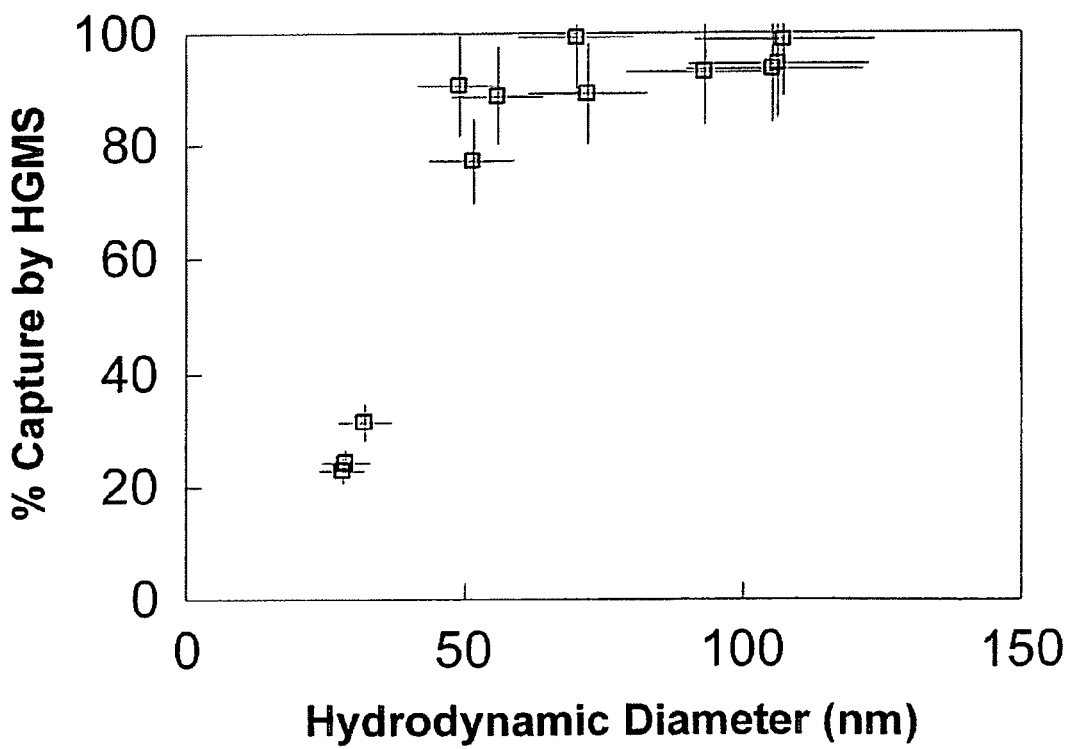
Figure 5E:
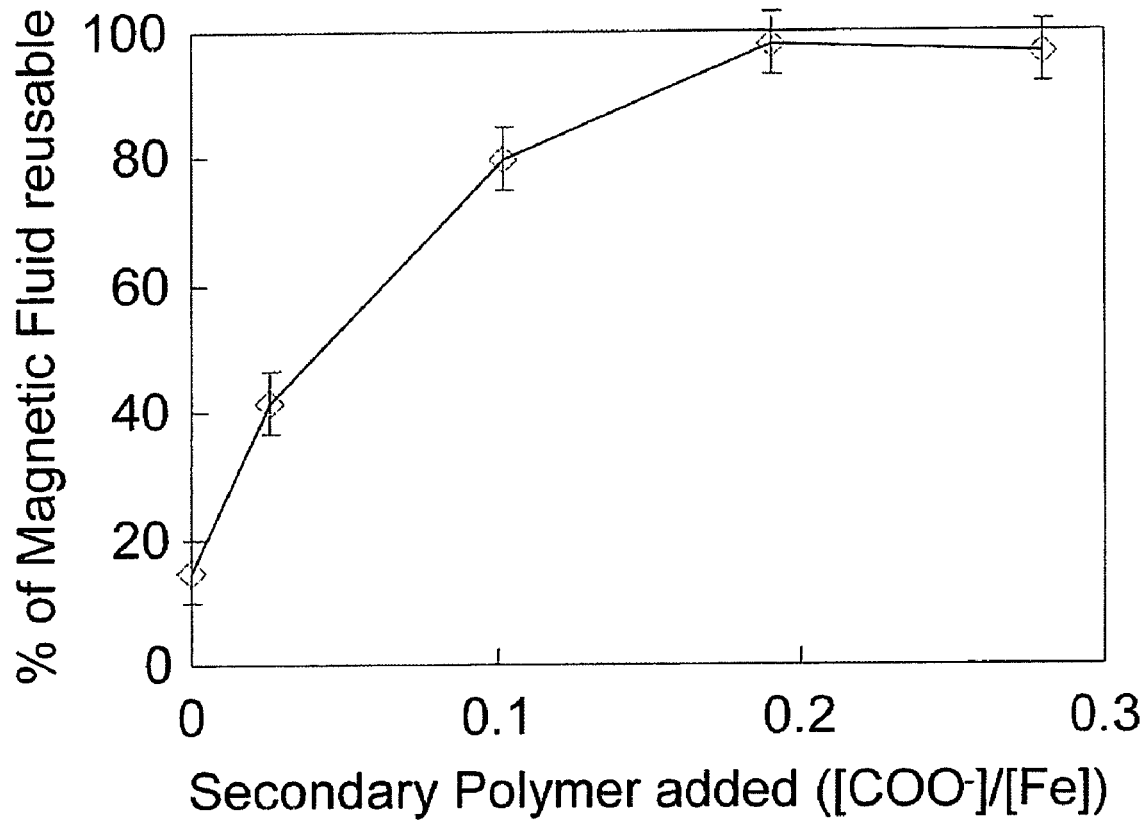
Figure 6:
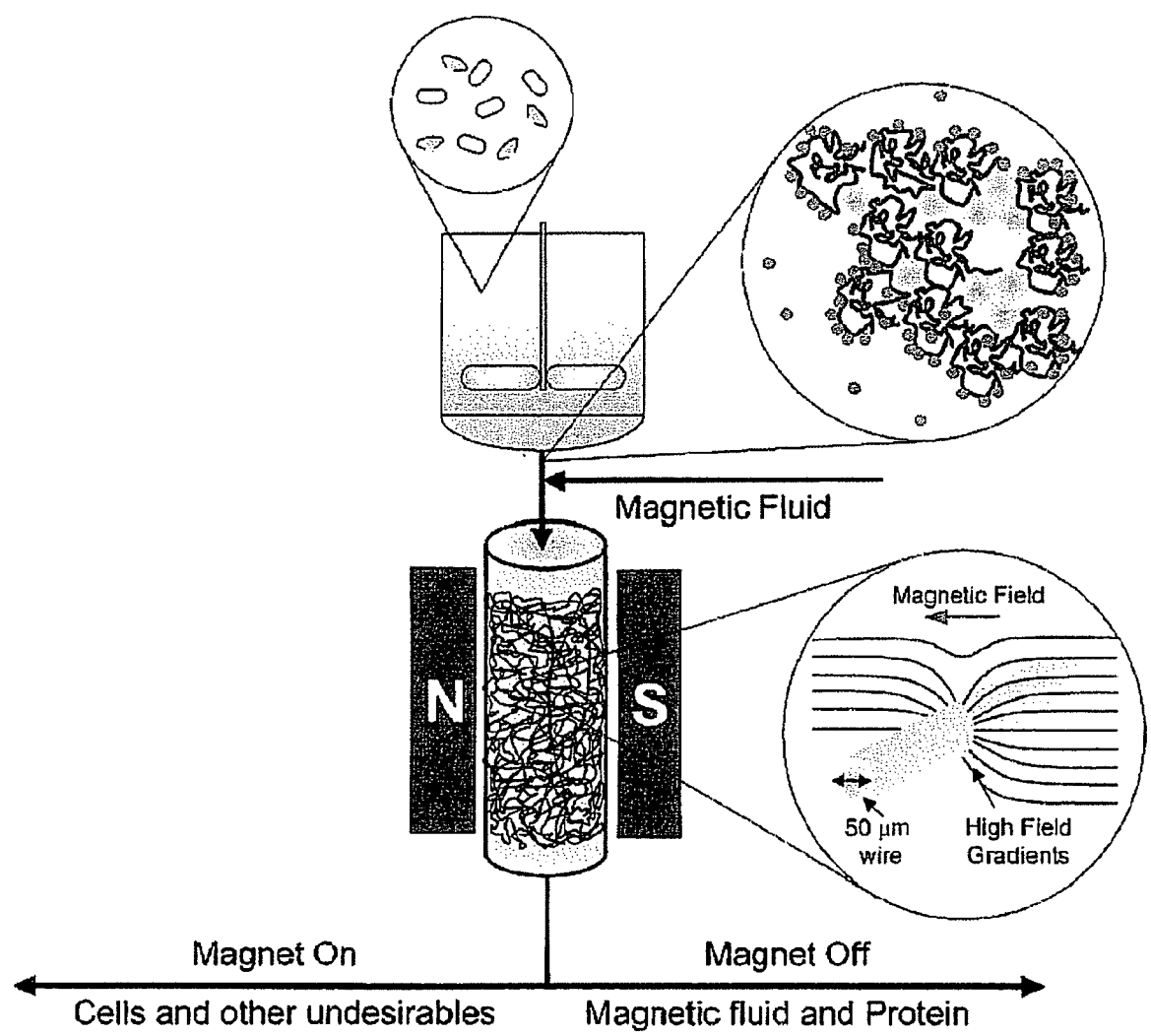

In another embodiment, solutions comprising the polymer-coated magnetic nanoclusters of this invention are reusable, which means, in one embodiment, which complete HGMS capture and resuspension stability may be accomplished. FIG. 5e, for example, shows the fraction of polymer-coated magnetic nanoclusters that were available for reuse after one protein adsorption and desorption cycle. In another embodiment, additional second polymer is added in order to increase the efficiency of reuse of the polymer-coated magnetic nanoclusters of this invention.

The following examples are presented in order to more fully illustrate some embodiments of the invention. They should, in no way be construed, however, as limiting the scope of the invention.

EXAMPLES

Example 1

Preparation of Polymer Coated Magnetic Nanoclusters

Magnetic nanoparticles were produced by chemical coprecipitation. 2.35 grams of iron (III) chloride hexahydrate and 0.86 g of iron (II) chloride tetrahydrate was added to 40 mL of deoxygenated water. The deoxygenation was achieved by bubbling nitrogen in a vigorously stirred 100 mL three-necked flask. The resulting $Fe^{3+}$ and $Fe^{2+}$ concentrations were 0.22 and 0.11M respectively, resulting in the required 2:1 ratio for magnetite ($Fe_3O_4$) production.

The nitrogen bubbling was ceased and the mixture was then heated over a range in temperature from 50 to 90° C., where 80° C. was found to be a desirable working temperature. A mixture of 5 mL of 28% ammonium hydroxide and various amount of polymer in water to a total added volume of 10 mL, typically 7 mmol of monomer units, was added. After 15 minutes, additional polymer, typically 4 mmol monomer basis, was added for additional coating. The reaction was allowed to proceed for 15 more minutes (30 minutes total) before cooling to room temperature. The magnetic fluid was then precipitated with 50-100 mL of Acetone, magnetically decanted, and resuspended in 30 mL of Milli-Q water and sonicated for 30 seconds with a Branson sonifier 450 at an output of 40%.

The overall scheme of magnetic nanoparticle production via chemical coprecipitation, is shown in FIG. 1. As exemplified above, iron ions are precipitated with a base in the presence of a polymer to form nanoclusters. A second polymer is added to stabilize the clusters.

Many different polymers were utilized in the preparation of the coated magnetic nanoparticles. Two classes of polymers exemplified herein, free radical random copolymers and graft copolymers are described in more detail. The first coating was performed with a random copolymer of acrylic acid, styrene sulfonic acid and vinyl sulfonic acid for negatively charged particles, a random copolymer of acrylic acid, vinylbenzyl trimethyl ammonium chloride and acrylamidopropyl trimethyl ammonium chloride for positively charged particles, and a graft copolymer with a backbone of acrylic acid and side chains of polyethylene oxide and polypropylene oxide was used to provide a hydrophobic domain and a hydophillic stabilizing shell.

Figure 2A:
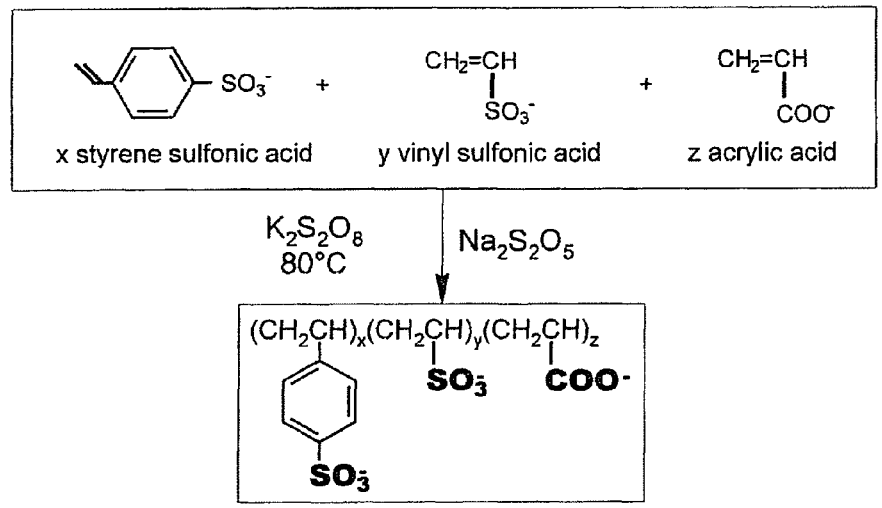

The first coating of negatively charged particles was accomplished with polymer 1, which consisted of styrene sulfonic acid, and the full incremental range of concentrations of 25% to 75%, vinyl sulfonic acid, with a full incremental range of concentrations of 25% to 50%, balance acrylic acid, preferably 25% with a molecular weight ranging from 2,000 to 300,000 preferably 5,000-10,000 was conducted. Polymer coating was such that the ratio of acrylic acid concentration/iron atom concentration was 0.1 to 0.6. A schematic depiction of polymer 1 is presented in FIG. 2a. The anionic polymer formed attaches to magnetite via its carboxylic acid functionality.

Figure 2B:
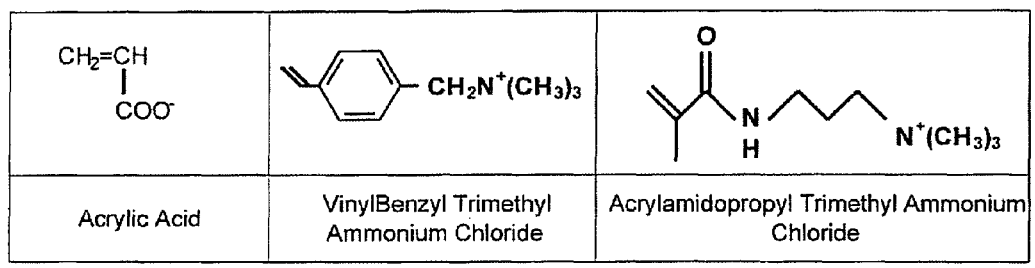

A first coating of positively charged particles was also accomplished with polymer 2, which consisted of vinyl benzyl trimethyl ammonium chloride or acrylamidopropyl trimethyl ammonium chloride, ranging in concentration from 25% to 90% with greater increments assessed at 70-80% and specifically at 75%, and balance acrylic acid. Polymer coating was such that the ratio of acrylic acid concentration/iron atom concentration was 0.1 to 0.6. A schematic depiction of polymer 2 is presented in FIG. 2b, where the synthesis procedure yielded an anionic polymer, which attached to magnetite via its carboxylic acid functionality.

Figure 2C:
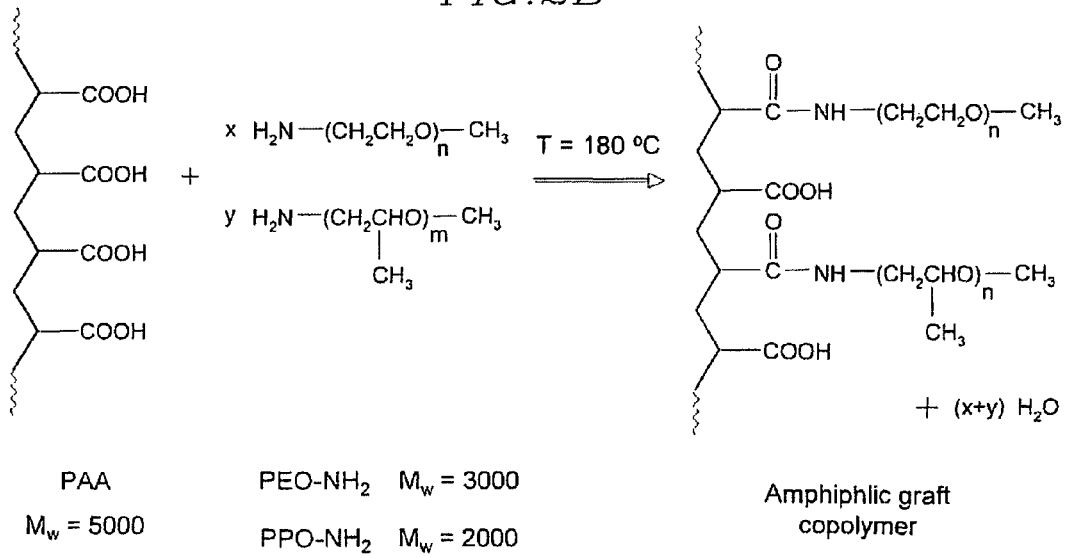

A first coating of particles with polymer 3, which consisted of a brush copolymer of PEO, 3,000 Mol. wt., (8-16% grafting, or the percent of acrylic acid repeat units reacted with PEO), or PPO, 2,000 Mol wt., (0-8% grafting), on PAA of 5000 Mol wt., in ranges of 0.25 to 1.25 grams/grams of magnetite, was also accomplished. A schematic depiction of polymer 3 is presented in FIG. 2c, illustrating graft copolymer synthesis by attaching amino-terminated PEO and PPO side chains to a PAA backbone via an amidation reaction. The majority of the COOH groups were left unreacted for subsequent attachment to magnetite nanoparticles.

In addition to the examples listed above, Table 1 lists additional first polymers used for coating of the magnetic nanoparticles:

TABLE 1

Additional Examples of First Polymers:

| Amount of Polymer (in grams) | Polymer MW | Composition |
| --- | --- | --- |
| 0.8 | 10,000 | 25% Acrylic acid, 50% Vinyl Sulfonic acid, 25% Styrene Sulfonic acid |
| 0.8 | 17,000 | 25% Acrylic acid, 25% Vinyl Sulfonic acid, 50% Styrene sulfonic acid |
| 0.8 | 25,000 | 25% Acrylic acid, 75% Styrene sulfonic acid |
| 1.0 | 2,000 | 20% Acrylic acid, 80% Vinyl Sulfonic acid |
| 0.8 | 2,000 | 30% Acrylic acid, 70% Vinyl Sulfonic acid |
| 0.6 | 2,000 | 40% Acrylic acid, 60% Vinyl Sulfonic acid |
| 1.0 | 15,000 | 25% Acrylic acid, 75% acrylamidopropyltrimethyl ammoniumchloride |
| 1.0 | 25,000 | 25% acrylic acid, 75% vinylbenzyl trimethyl ammonium chloride |
| 0.25 | 38000 | 5000 mol. wt. poly (acrylic acid) backbone 16% grafting of 3000 MW poly(ethylene oxide) |
| 0.50 | 38000 | 5000 mol. wt. poly (acrylic acid) backbone 16% grafting of 3000 MW poly(ethylene oxide) |
| 0.75 | 38000 | 5000 mol. wt. poly (acrylic acid) backbone 16% grafting of 3000 MW poly(ethylene oxide) |
| 1.00 | 38000 | 5000 mol. wt. poly (acrylic acid) backbone 16% grafting of 3000 MW poly(ethylene oxide) |
| 0.25 | 33000 | 5000 MW poly (acrylic acid) backbone 8% grafting of 3000 MW poly(ethylene oxide); 8% grafting of 2000 MW poly(propylene oxide) |
| 0.50 | 33000 | 5000 MW poly (acrylic acid) backbone 8% grafting of 3000 MW poly(ethylene oxide); 8% grafting of 2000 MW poly(propylene oxide) |
| 0.75 | 33000 | 5000 MW poly (acrylic acid) backbone 8% grafting of 3000 MW poly(ethylene oxide); 8% grafting of 2000 MW poly(propylene oxide) |
| 1.00 | 33000 | 5000 MW poly (acrylic acid) backbone 8% grafting of 3000 MW poly(ethylene oxide); 8% grafting of 2000 MW poly(propylene oxide) |
| 1.00 | 36000 | 20% acrylic acid, 80% vinylbenzyl trimethylammonium chloride |
| 1.00 | 36000 | 30% acrylic acid, 70% vinylbenzyl trimethylammonium chloride |
| 1.00 | 36000 | 40% acrylic acid, 60% vinylbenzyl trimethylammonium chloride |
| 1.00 | 36000 | 50% acrylic acid, 50% viriylbenzyl trimethylammonium chloride |
| 1.00 | 36000 | 75% acrylic acid, 25% vinylbenzyl trimethylammonium chloride |
| 0.70 | 30000 | 75% acrylic acid, 25% styrene sulfonic acid |
| 0.70 | 90000 | " |
| 0.90 | 2000 | 30% acrylic acid, 70% vinylsulfonic acid |
| 1.1 | 3000 | 25% Acrylic acid, 75% Styrene Sulfonic acid |
| 1.1 | 5000 | " |
| 1.1 | 12000 | " |
| 1.1 | 16000 | " |
| 1.1 | 23000 | " |
| 1.1 | 44000 | " |
| 1.1 | 102000 | " |
| 1.1 | 210000 | " |
| 1.1 | 300000 | " |
| 1.0 | 3000 | 25% Acrylic acid, 25% Vinyl Sulfonic acid, 50% Styrene Sulfonic Acid |
| 1.0 | 5000 | " |

TABLE 1-continued

Additional Examples of First Polymers:

| Amount of Polymer (in grams) | Polymer MW | Composition |
|---|---|---|
| 1.0 | 9000 | " |
| 1.0 | 12000 | " |
| 1.0 | 17000 | " |
| 1.0 | 32000 | " |
| 1.0 | 70000 | " |
| 0.8 | 2000 | 25% Acrylic acid, 50% Vinyl Sulfonic acid, 25% Styrene Sulfonic Acid |
| 0.8 | 4000 | " |
| 0.8 | 5000 | " |
| 0.8 | 7000 | " |
| 0.8 | 10000 | " |
| 0.8 | 19000 | " |
| 0.8 | 38000 | " |
| 0.8 | 6000 | 50% Acrylic acid, 25% Vinyl Sulfonic acid, 25% Styrene Sulfonic Acid |
| 0.8 | 7000 | " |
| 0.8 | 11000 | " |
| 0.8 | 22000 | " |
| 0.8 | 49000 | " |
| 0.8 | 117000 | " |
| 0.9 | 8000 | 50% Acrylic acid, 50% Styrene Sulfonic Acid |
| 0.9 | 11000 | " |
| 0.9 | 16000 | " |
| 0.9 | 21000 | " |
| 0.9 | 30000 | " |
| 0.9 | 55000 | " |
| 0.9 | 109000 | " |
| 0.9 | 162000 | " |
| 0.9 | 193000 | " |
| 0.9 | 227000 | " |
| 0.9 | 248000 | " |
| 0.7 | 1000 | 30% Acrylic acid, 70% Vinyl Sulfonic acid |
| 0.7 | 2000 | |
| 0.7 | 3000 | |
| 0.7 | 4000 | |
| 0.7 | 5000 | |
| 0.7 | 6000 | |
| 0.7 | 7000 | |
| 0.7 | 11000 | |
| 1.1 | 2000 | 25% Acrylic acid, 75% acrylamidopropyl trimethyl ammoniumchloride |
| 1.1 | 3000 | |
| 1.1 | 5000 | |
| 1.1 | 10000 | |
| 1.1 | 19000 | |
| 1.1 | 35000 | |
| 1.1 | 260000 | |
| 1.7 | 11000 | 25% Acrylic acid, 75% vinyl benzyl trimethyl ammonium chloride |
| 1.7 | 16000 | |
| 1.7 | 36000 | |
| 1.7 | 170000 | |

*amount of first polymer is per gram of magnetite

As can be seen from Table 1, multi-polymer-coated magnetic nanoparticles were constructed wherein the first polymer comprised varying concentrations of components, with molecular weight held as a constant, or vice versa. Furthermore, the multi-polymer-coated magnetic nanoparticles may be produced at a variety of different temperatures (Table 2), as well.

TABLE 2

| Amount of Polymer (in grams) | Polymer MW | Composition | Temperature |
|---|---|---|---|
| 0.90 | 2000 | 30% acrylic acid, 70% vinylsulfonic acid | 50° C. |
| 0.90 | 2000 | 30% acrylic acid, 70% vinylsulfonic acid | 60° C. |
| 0.90 | 2000 | 30% acrylic acid, 70% vinylsulfonic acid | 70° C. |
| 0.90 | 2000 | 30% acrylic acid, 70% vinylsulfonic acid | 90° C. |

A second coating of polymer 4, which consisted of poly acrylic acid was accomplished, with the poly acrylic acid molecular weight ranging from 2 kDa to 250 kDa, small increments within the range utilized, for example, 5 kDa, at a concentration of 0.1 to 0.5 grams, preferably 0.3 grams per gram magnetite. An alternative second coating was utilized, that of polymer 5, which consisted of a copolymer of AA and VSA (25-50%), which had a molecular weight of 10,000, specifically 50% and 25%, at a concentration ranging between 0.1 to 0.5 grams, for example, 0.4 grams per gram magnetite were constructed.

In addition to the examples listed above, Table 3 lists additional second polymers used for coating of the magnetic nanoparticles:

TABLE 3

Additional Examples of Second Polymers:

| Amount of Polymer (in grams) | Polymer MW | Composition |
|---|---|---|
| 0.3 | 5,000 | poly (acrylic acid) |
| 0.3 | 8,000 | poly (acrylic acid) |
| 0.3 | 15,000 | poly (acrylic acid) |
| 0.3 | 30,000 | poly (acrylic acid) |
| 0.3 | 50,000 | poly (acrylic acid) |
| 0.3 | 70,000 | poly (acrylic acid) |
| 0.3 | 100,000 | poly (acrylic acid) |
| 0.3 | 250,000 | poly (acrylic acid) |
| 0.3 | 2000 | poly (acrylic acid) |
| 0.5 | " | poly (acrylic acid) |
| 0.1 | 5000 | poly (acrylic acid) |
| 0.2 | " | poly (acrylic acid) |
| 0.3 | " | poly (acrylic acid) |
| 0.5 | " | poly (acrylic acid) |
| 0.1 | 8000 | poly (acrylic acid) |
| 0.2 | " | poly (acrylic acid) |
| 0.3 | " | poly (acrylic acid) |
| 0.1 | 15000 | poly (acrylic acid) |
| 0.2 | " | poly (acrylic acid) |
| 0.3 | " | poly (acrylic acid) |
| 0.1 | 30000 | poly (acrylic acid) |
| 0.2 | " | poly (acrylic acid) |
| 0.3 | " | poly (acrylic acid) |
| 0.1 | 50000 | poly (acrylic acid) |
| 0.2 | " | poly (acrylic acid) |
| 0.3 | " | poly (acrylic acid) |
| 0.1 | 70000 | poly (acrylic acid) |
| 0.2 | " | poly (acrylic acid) |
| 0.3 | " | poly (acrylic acid) |
| 0.1 | 100000 | poly (acrylic acid) |
| 0.2 | " | poly (acrylic acid) |
| 0.3 | " | poly (acrylic acid) |
| 0.3 | 250000 | poly (acrylic acid) |
| 0.03 | 10000 | 75% acrylic acid, 25% vinyl sulfonic acid |
| 0.05 | | |
| 0.10 | | |
| 0.19 | | |
| 0.28 | | |
| 0.40 | | |
| 0.40 | 10000 | 50% acrylic acid, 25% vinyl sulfonic acid |
| 0.25 | 38000 | 5000 MW poly (acrylic acid) backbone 16% grafting of 3000 MW poly(ethylene oxide) |
| 0.50 | 38000 | |
| 0.75 | 38000 | |
| 1.00 | 38000 | |
| 0.25 | 33000 | 5000 MW poly (acrylic acid) backbone 8% grafting of 3000 MW poly(ethylene oxide); 8% grafting of 2000 MW poly (propylene oxide) |
| 0.50 | 33000 | |
| 0.75 | 33000 | |
| 1.00 | 33000 | |
| 1.0 | 10000 | 25% acrylic acid, 75% acrylamidopropyltrimethyl ammonium chloride |

As is evident from Table 3, multi-polymer-coated magnetic nanoparticles were constructed wherein the second polymer comprised a variety of components, with variations including that the molecular weight was held as a constant, while the amount of polymer added was varied, or vice versa.

Multiple particles were synthesized by these methods, including those with a first coating of polymer 1 and a second coating of polymer 3, 4 or 5, or a first and second coating of the particles with polymer 2, or a first coating of polymer 3, with a second coating of polymer 3, 4 or 5.

Example 2

Magnetic Nanocluster Size Control as a Function of First Polymer Attachment Materials and Experimental Methods Magnetic nanoparticles were prepared as follows: 2.35 grams of iron (III) chloride hexahydrate and 0.86 g of iron (II) chloride tetrahydrate was added to 40 mL of deoxygenated water. The resulting Fe3+ and Fe2+ concentrations were 0.22 and 0.11M respectively. The mixture was then heated to 80° C.

First polymers used for the formation of various multi-polymer coated magnetic nanoparticles is as listed in Table 4.

TABLE 4

First Polymers Used For Formation Of Multi-Polymer Coated Magnetic Nanoparticles:

| Amount of Polymer (in grams) | Polymer MW | Composition |
|---|---|---|
| 0.4-1.4 | 10,000 | 25% Acrylic acid, 50% Vinyl Sulfonic acid, 25% Styrene Sulfonic acid |
| 0.4-1.6 | 17,000 | 25% Acrylic acid, 25% Vinyl Sulfonic acid, 50% Styrene sulfonic acid |
| 0.4-1.4 | 11,000 | 50% acrylic acid, 25% vinyl sulfonic acid, 25% styrene sulfonic acid |
| 0.5-1.8 | 25,000 | 25% Acrylic acid, 75% Styrene sulfonic acid |
| 0.6-1.2 | 2,000 | 20% Acrylic acid, 80% Vinyl Sulfonic acid |
| 0.2-1.1 | 2,000 | 30% Acrylic acid, 70% Vinyl Sulfonic acid |
| 0.2-1.1 | 2,000 | 40% Acrylic acid, 60% Vinyl Sulfonic acid |

A mixture of 5 mL of 28% ammonium hydroxide and varied amounts of polymer, from 0.06 mol COO-/mol Fe ions to 0.55 mol COO-/mol Fe ions.

After 15 minutes, the second polymer, 0.3 grams of 5000 PAA, was added for additional coating. The reaction was allowed to proceed for 15 more minutes (30 minutes total) before cooling to room temperature. The magnetic fluid was then precipitated with 50-100 mL of Acetone, magnetically decanted, and resuspended in 30 mL of Milli-Q water and sonicated for 30 seconds with a Branson sonifier 450 at an output of 40%. Dynamic light scattering (DLS) experiments were performed with the Brookhaven BI-200SM light scattering system at a measurement angle of 90°.

Results

Figure 3:
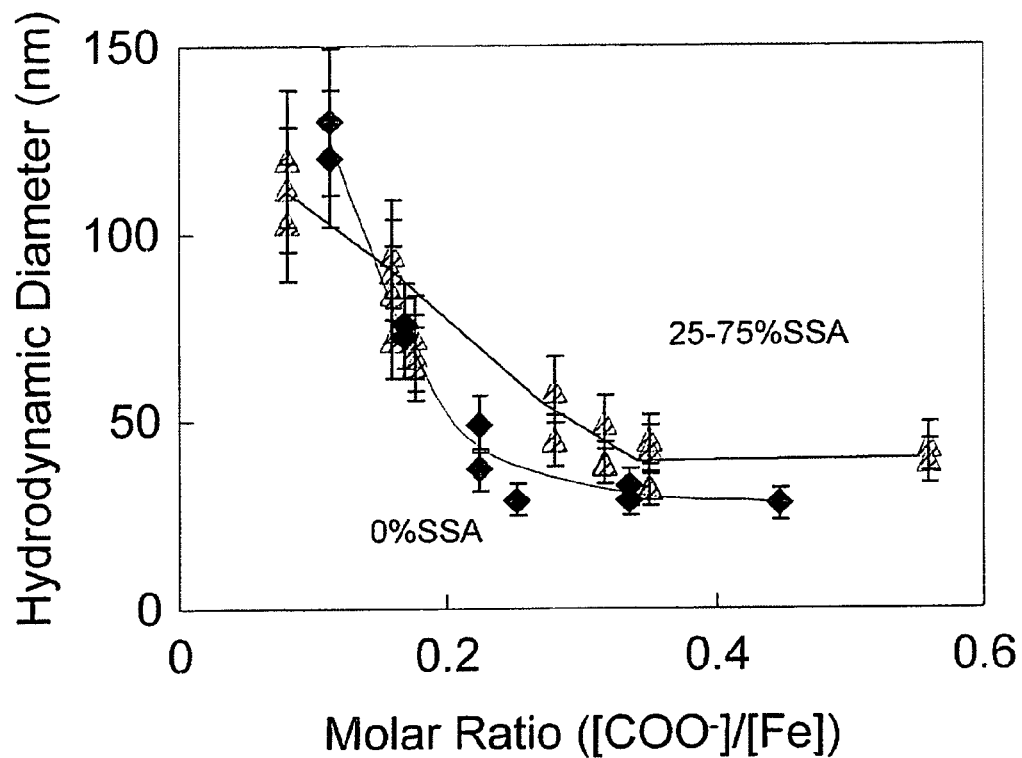

HGMS capture results are optimal when cluster size is between 50-70 nm. In order to determine the effect of the first polymer on the cluster size, varying amounts of polymer, as indicated in Table 3 were added initially with the base. Limiting the amount of polymer 1 produced the optimal cluster sizes mentioned (FIG. 3). Specifically, limiting the amount of polymer 1 to produce a molar ratio of the concentration of iron chelating groups (carboxylic acid) in polymer 1, versus the amount of iron atoms in solution to about 0.14-0.2, produced the desirable cluster size (FIG. 3). Magnetic cluster size control is affected, in this case, by controlling the ratio in polymers in solution, which comprise the first coating, while addition of a secondary polymer of <15 kDa after a few minutes had no effect on particle size. The cluster size for clusters made with polymers containing the hydrophobic Styrene Sulfonic acid group fell along one curve, while the clusters formed with no hydrophobic groups fell along a different curve.

Example 3

Magnetic Nanocluster Size Control as a Function of Second Polymer Attachment Materials and Experimental Methods Magnetic nanoparticles were prepared as in Example 2, and coated with 0.8 grams of 10 kDa-sized first polymer, composed of 25% Acrylic acid, 50% Vinyl Sulfonic acid, and 25% Styrene Sulfonic acid, via method described. Second polymer coating was similarly accomplished, in each case using 0.3 grams of the polymer, with varied molecular weights, as listed in Table 5, as well as samples without second polymer coating. Dynamic light scattering was accomplished as in Example 2.

TABLE 5

Second Polymers Used For Formation Of Multi-Polymer Coated Magnetic Nanoparticles:

| Polymer MW | Composition |
|---|---|
| 5,000 | polyacrylic acid |
| 8,000 | polyacrylic acid |
| 15,000 | polyacrylic acid |
| 30,000 | polyacrylic acid |
| 50,000 | polyacrylic acid |
| 70,000 | polyacrylic acid |
| 100,000 | polyacrylic acid |
| 250,000 | polyacrylic acid |

Results

Figure 4:
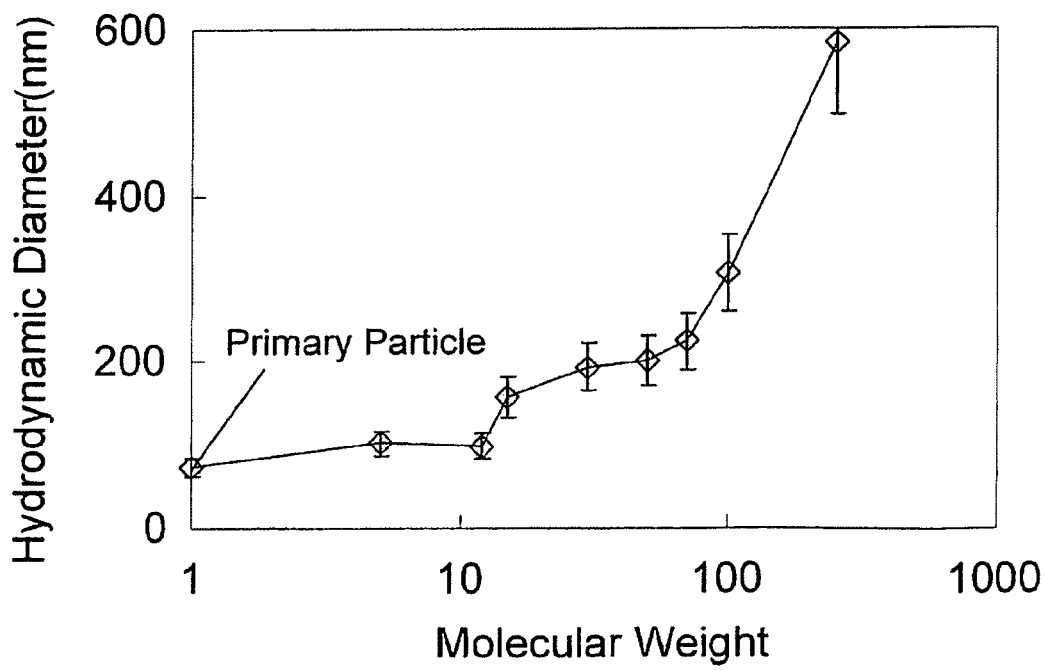

When the molecular size of the secondary coating was relatively small (<15 kDa), the size of the clusters with a secondary PAA coating was not significantly different than those without any secondary coating (FIG. 4). When the secondary coating was of a larger molecular size, however, the clusters were bound together and formed larger aggregates.

Example 4

Protein Purification Using Polymer Coated Magnetic Nanoclusters Materials and Experimental Methods Nanoclusters were assembled as described herein, with the first coating consisting of 0.8 grams or 10 kDa in size polymer, consisting of 25% acrylic acid, 50% Vinyl sulfonic acid and 25% Styrene sulfonic acid. The second coating consisted of 0.3 grams, 5 kDa in size polymer 2, consisting of poly (acrylic acid).

Cytochrome-C (pI=10.3) at a concentration of 0.2-1.4 mg/ml was mixed with washed (excess polymer and salts removed) magnetic nanoclusters to a final concentration of 1.0 mg/mL in 5 mM TES buffer at a pH of 7-8. Samples were equilibrated for 10 minutes and passed through an HGMS column, where unbound protein was collected. The magnetic fluid was then resuspended with 0.5M NaCl and passed through the column again, collecting the eluted protein. The magnetic fluid was then resuspended in pure water. Bound and eluted protein concentrations were monitored by absorbance at 412 nm.

High gradient magnetic separation (HGMS) experiments were performed with a Model L-1CN Frantz Canister Separator, supplied by S.G. Frantz Co., Inc. (Trenton, N.J.). The HGMS system consisted of a cylindrical glass column with an internal radius of 0.332 cm and a length of 5.8 cm (a volume of 2 $cm^3$) that was packed with type 430 fine-grade stainless steel wool (40-66 mm diameter) also supplied by S.G. Frantz Co., Inc. The packing occupied 0.25 $cm^3$, resulting in a packing fraction of 12.5%. A magnetic field was generated with an attached electromagnet with the direction of the magnetic field transverse to the direction of flow through the column. The flux density generated between the two plates was 1.3 T, as measured with a handheld magnetometer.

Magnetic filtration of the particles was performed by passing 20 mL of dilute magnetic fluid through the column with the electromagnet on. This volume is equal to 12 column volumes, thus the particles captured were assumed to be permanently captured. The liquid was pumped at 1.4 mL/min with a peristaltic pump. The magnet was then turned off and 20 mL of water was passed through the column to collect and resuspend the washed particles. The fraction of escaping particles during magnetic washing was determined by chemical iron titration [Yoe, J. H.; Jones, L. Colorimetric Determination of Iron with Disodium-1,2-dihydroxybenzene-3,5-disulfonate. Ind. Eng. Chem. 1944, 16, 111-115] that measured the $Fe_3O_4$ concentration in the filtrate.

Results

In order to determine whether HGMS can effectively be used for the multi-polymer-coated magnetic nanoparticles described, binding isotherms were assessed. The fraction of bound protein as a function of unbound concentration is shown in FIG. 5a, where the maximum capacity was 640 mg/g magnetic fluid. With a particle density of 1.3 g/ml, this equals 840 mg/ml of support, which is considerably higher than the maximum binding capacity, about 150 mg/mL, of porous supports. The capacity decreases linearly with $I^{0.5}$ as shown in FIG. 5b, as would be expected for an electrostatic interaction. The elution of the proteins at 0.5 NaCl is nearly quantitative, as shown in FIG. 5c.

In order to determine that multi-polymer-coated magnetic nanoparticles provide for efficient HGMS capture, HGMS filtration was performed on many of the magnetic fluids produced. The capture of the particles is shown in FIG. 5d as a function of particle size for both clusters formed by core-to-core contact, and for particles that are attached by polymer bridges. From FIG. 5d, it can be seen that capture is nearly complete for clusters larger than about 60 nm when formed by core-to-core contact.

It was also of interest to determine whether the fluids may be reusable, i.e., that complete HGMS capture and resuspension stability may be accomplished. Since proteins act as multivalent ions, and thus tend to aggregate colloids just as high salt concentrations do, a high critical coagulation concentration is required for the particles to be stable enough for reuse. FIG. 5e shows the fraction of particles that are available for reuse after one protein adsorption and desorption cycle as more secondary polymer is added. Of all combinations tested in the current system, 18% reuse was the maximum, while complete reuse was possible when sufficient 2nd polymer was added.

Example 5

Purification of Expressed Protein

The recovery of proteins from unclarified fermentation broth can be accomplished via a scheme, as outlined in FIG.

6. Multi-polymer-coated magnetic nanoparticles may be produced according to any of the embodiments listed herein, and the magnetic nanoparticles may be added directly to the fermentation broth, where desired proteins are adsorbed. The solution is then run through a high gradient magnetic separation (HGMS) device to capture the magnetic clusters along with the desired protein.

Example 6

Protein Purification from Whole Cell Broth

In order to determine whether protein recovery from whole cell broth may be accomplished with magnetic nanoclusters, *Pichia Pastoris* cells expressing drosomycin were incubated for 16 hours in a shake flask with BMGY medium (1% yeast extract, 2% peptone, 1.34% yeast nitrogen base, $4 \times 10^{-5}$% biotin, 1% glycerol, 100 mM potassium phosphate, pH 5.0) at 30° C. The fermentation was performed at 30° C. using a 1 vvm air-flow rate 155 supplemented with pure oxygen to maintain a dissolved oxygen content greater than 20%. The pH was maintained at 5 with ammonium hydroxide (30% w/v). Agitation was performed at the maximum speed where excessive foaming was not observed, typically 500 rpm.

Fermentation broth was centrifuged in an Eppendorf 5810R centrifuge at 4000 rpm for 30 minutes to remove cells. The clarified broth was re-diluted to account for volume loss due to cell volume. The pH of the broth was then adjusted, typically to a value of 3, with 10M HCl. 4 mL of the fermentation broth were mixed with 1 mL of magnetic fluid of varying magnetite content. The mixture was then passed through an HGMS column, where the unbound fraction was collected. With the magnet still on, the column was washed with one column volume of 50 mM phosphate buffer (pH=3). The magnet was then turned off and the nanoclusters were eluted with the desired elution buffer. The nanoclusters were again captured by HGMS, and the eluted protein was collected.

Figure 7A:
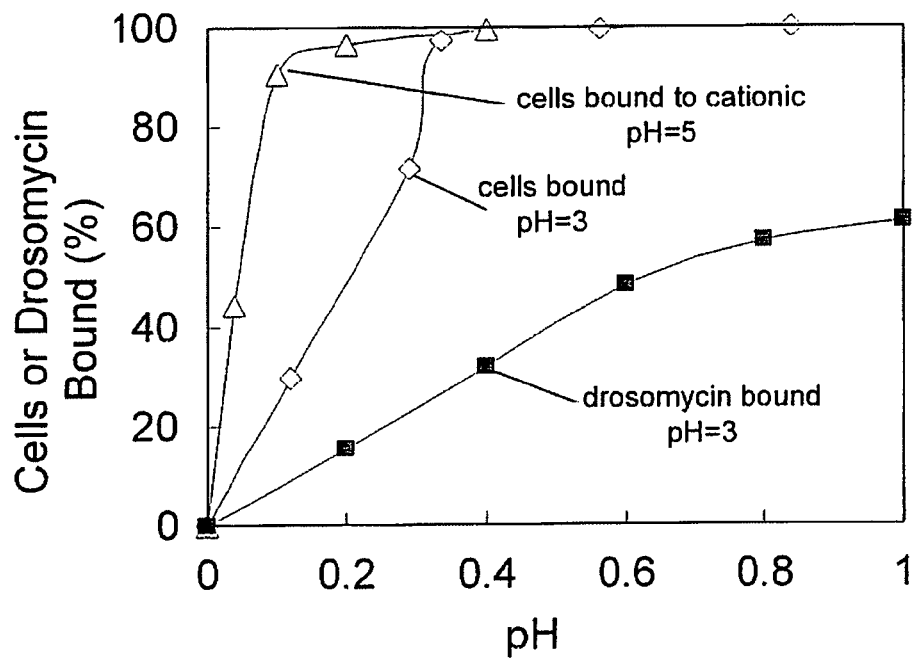

Nanocluster binding to cells was stronger than to the expressed protein, drosomycin (FIG. 7A), providing a versatile application for cell separation. Both anionic and cationic nanoclusters were tested in this context, in order to determine whether the overall cell surface charge played a role in binding, and anionic nanocluster use resulted in stronger binding. Thus the heterogeneous cell surface charge enables nanoclusters of both charges to bind.

Figure 7B:
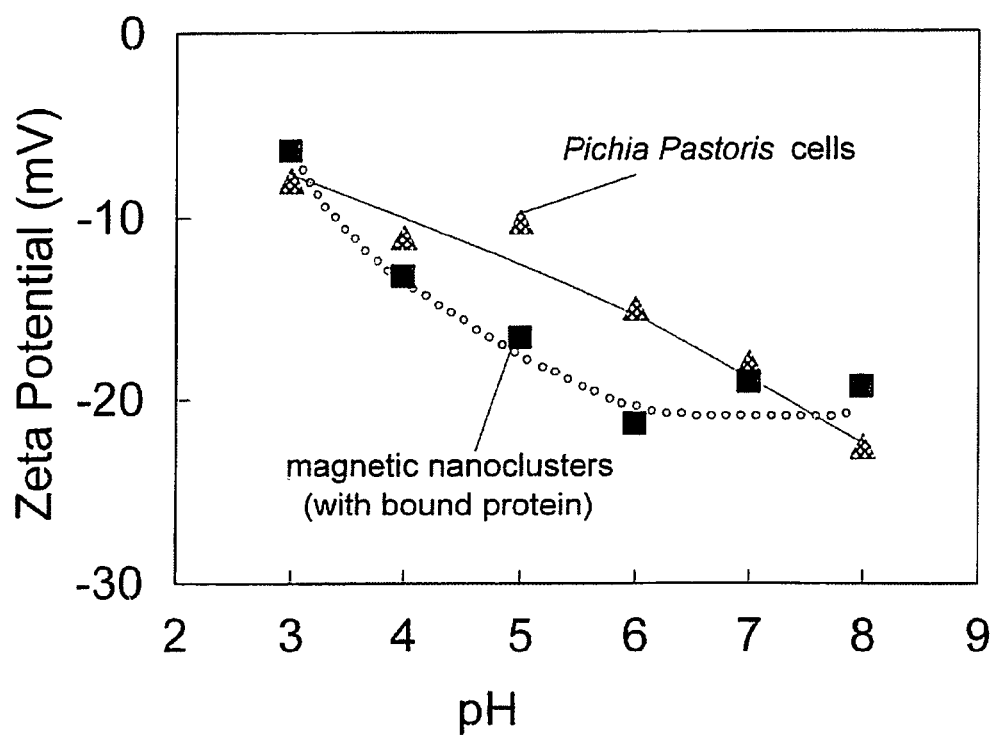
Figure 8A:
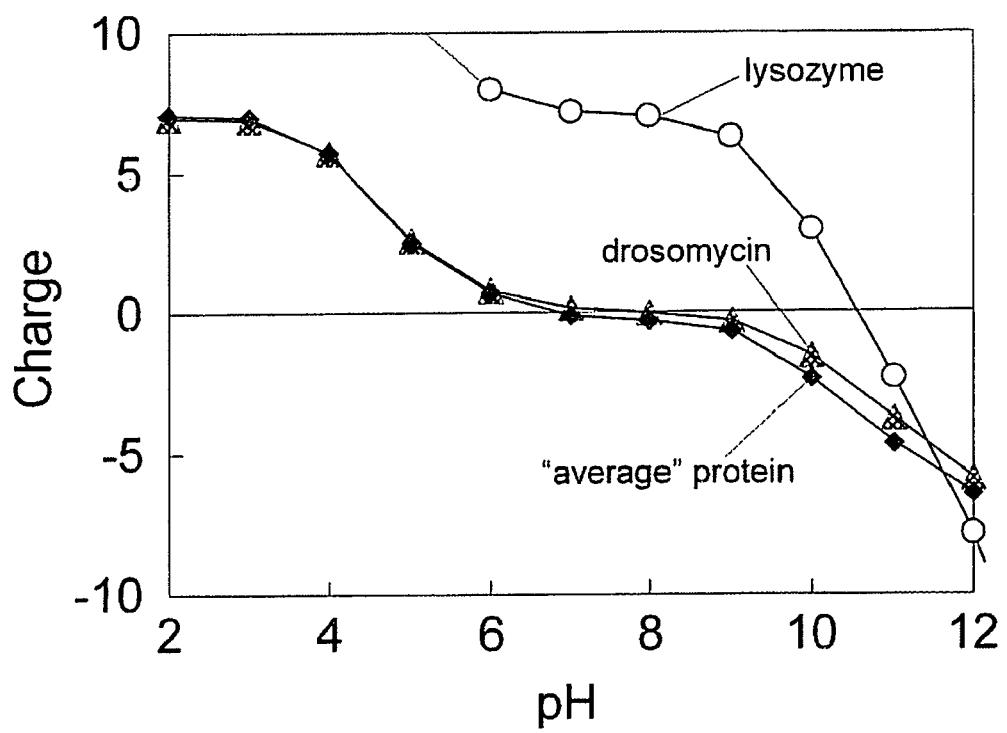

The zeta potential of the cells and the nanoclusters was measured, in order to delineate the binding mechanism. FIG. 7B demonstrates that both the cells and nanoclusters were negatively charged at all observed, relevant pH values, indicating that the binding was due to local positive charges, and not to the overall cell charge. Yeast cell surfaces are a complex mixture of polysaccharides, proteins and phospholipids, with the positively charged groups on the cell surface most likely being protein. Since protein charge is highly dependent on pH, the binding of nanoclusters to cells is expected to be a strong function of pH. The charge vs. pH of an "average protein" is shown in FIG. 8A, which is simply assuming a protein of the same size as drosomycin, but with amino acid composition equal to the overall abundance of amino acids in *E. coli* (Lehninger, A. L., *Biochemistry*. 2nd edition ed. 1975, New York: Worth Publishers). The curves are theoretical, obtained assuming that the amino acid residues have the same pKa values as the isolated amino acids. Note that drosomycin does not have a significantly different charge from that of an average protein, and thus is a difficult target to bind without binding other proteins, including cell surface proteins. Strongly cationic proteins, such as lysozyme, show significantly different charge vs. pH behavior.

Figure 8B:
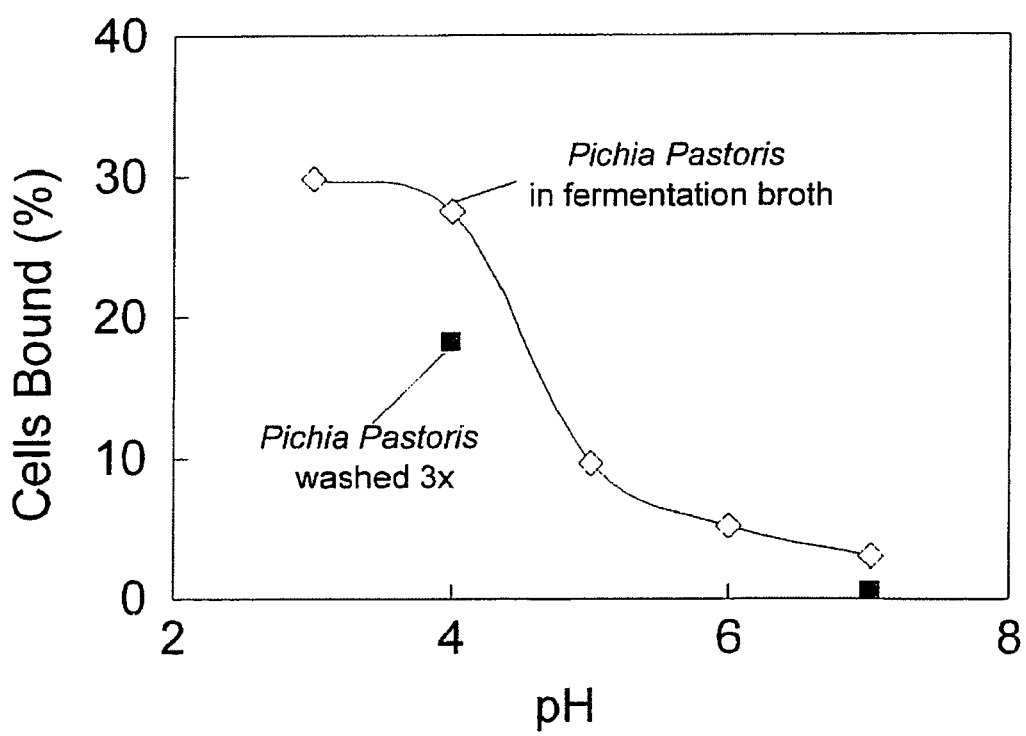

The binding of the nanoclusters to the cells exhibited strong pH dependence, indicating that the charged group that bound to the nanocluster was most likely a protein. The pH dependence of binding, as shown in FIG. 8B, mirrors the charge of drosomycin and the "average protein".

Cells were isolated from all extracellular proteins by centrifugation and washing with carbonate buffer at a pH of 10 several times prior to re-suspension in protein free buffer, to eliminate the possibility that the clustering was due to the bound drosomycin serving as a cross linking agent. Under these conditions, the nanoclusters still bound strongly to the cells at low pH and weakly at high pH, indicating that the binding protein was part of the cell surface.

Figure 8C:
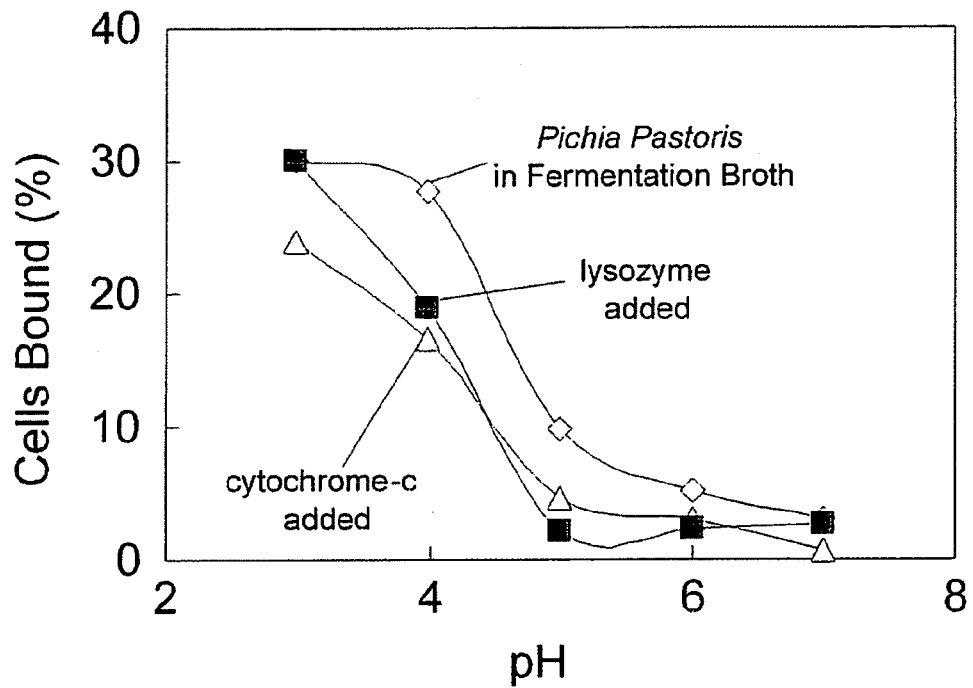

To further verify that nanocluster cross-linking was not the dominant mechanism of cell-nanocluster binding, lysozyme and cytochrome-c were added to the fermentation broth. When either of these proteins was present, particularly lysozyme, the nanoclusters still agglomerated reversibly due to protein mediated crosslinking at high pH values. However at higher pH with adsorbing proteins present, the nanoclusters do not bind to the cells, as shown in FIG. 8C, and in fact the fraction of cells bound to nanoclusters is slightly reduced when these proteins are present. It appears that the dominant mechanism for binding of nanoclusters to cells is due to a surface protein of *Pichia pastoris* that binds under the same conditions as drosomycin.

Since the nanocluster-cell binding was due to protein binding, several attempts were made to improve the specificity of the binding for drosomycin. The first attempt was to use surfactants, such as sodium dodecyl sulfate, Tween 20 and Pluronic F-68 to reduce hydrophobic interactions. The results are summarized in Table 6, and it was found that surfactant addition was not an effective method of reducing cell-nanoparticle binding. Several other attempts such as using polar organic compounds, and with other magnetic fluid synthesis routes to sterically hinder protein adsorption were also attempted, but it was found that the cell surface protein bound more strongly than drosomycin under the conditions evaluated.

TABLE 6

Cell binding with added surfactant.

| Additive | Amount (wt %) | Cells Trapped (%) |
|---|---|---|
| None | (—) | 98.3 |
| Pluronic F68 | 0.1% | 99.3 |
| Tween-20 | 0.1% | 98.8 |
| SDS | 0.1% | 99.3 |
| SDS | 1.0% | 99.2 |

Example 7

Model for Nanocluster-Cell Binding

Example 6 indicated that a cell surface protein was responsible for the nanoparticle-cell binding, yet it is surprising that a small local positively charged patch can be sufficient for binding when the overall cell charge is negative. Mammalian cell binding to negatively charged chromatography supports at low pH has been reported, though yeast cells do not typically bind to cation exchange resins. The most likely reason for the increased binding of nanoclusters was due to the much higher curvature of the nanoclusters than chromatography supports. A simple model was devised for this interaction, based on the electrostatic interaction between charged spheres of different diameter, outlined below and shown schematically in FIG. 9.

The interaction between charged spheres of different size can be expressed with the equations given by Hogg et al. (Trans. Faraday Soc. 1966, 62: 1638) for interactions between clusters and single nanoclusters, $$u_e = 4\pi\varepsilon\varepsilon_0 \left(\frac{R_1 R_2}{R_1 + R_2}\right)(\psi^\infty)^2 \ln(1 + \exp(-\kappa s)) \quad (7\text{-}1)$$

where s is the surface separation distance between the particles, $\psi^\infty$ is the surface potential of an isolated particle, which is approximately the zeta potential of the particle, $\kappa$ is the inverse debye length, $\varepsilon$ is the dielectric constant, and $\varepsilon_0$ is the permitivity of free space and $R_1$ and $R_2$ are the interacting particle diameters. By inspection of equation 7-1, the electrostatic potential is dominated by the smaller particle.

For example if $R_1 \gg R_2$, then the bracketed term $$\left(\frac{R_1 R_2}{R_1 + R_2}\right) \approx R_2.$$

If we assume that the protein is a sphere with a diameter of 4 nm, the nanocluster is a sphere with a radius of 50 nm, and the cell has a diameter of 5 μm, and that the surface of the protein protrudes 2 nm from the cell surface, the interaction energy can be calculated. The cell and nanoparticle charge ($\psi^\infty$) are assumed to be −30 mV while the protein has a charge of 30 mV. The ionic strength has been assumed to be 0.4, and the total potential is assumed to be simply the interaction of the nanocluster and an isolated cell added to the potential of the nanocluster and an isolated protein.

The results of this simple model are shown in FIG. 10. The interaction energy for the cell and protein with the nanocluster is attractive and binding is expected. When the diameter of the nanoparticle is replaced with the diameter of a typical chromatography support, 100 μm, the interaction becomes strongly repulsive. The attractive interactions between the protein and both the nanocluster and the chromatography bead are essentially the same, as both are much larger than the protein and the attractive force scales with the protein radius. However the repulsive force between the cell and the nanocluster scales with the nanocluster radius and is much smaller than the repulsion between the cell and the chromatography support, which scales with the cell diameter.

This simple model result indicates that, due to the small size of the nanocluster and high ionic strength of fermentation broth, nanoclusters will be attracted to cell surface proteins nearly as strongly as to free proteins. Under the set of conditions examined, only if the targeted protein can be captured at conditions that do not attract cell surface proteins can the separation be performed in whole cell broth.

Purifying proteins which are not strongly cationic, such as drosomycin, from other extracellular proteins (binding many proteins and selectively eluting drosomycin) will not be effective in whole cell broth under the conditions evaluated, since cell surface proteins are also bound. This finding provides a basis for designing separations, indicating that very specific interactions between the particle and the desired protein must exist for one step purification. Due to the low hydrophobicity and nearly average charge vs. pH of drosomycin, it is unlikely that any conditions exist where drosomycin and only drosomycin is bound to a hydrophobic charged surface, without other surface modification. However certain proteins deviate much more from average behavior and can be separated from whole cell broth in a single step with these unmodified nanoclusters.

*Pichia pastoris* broth adjusted to a pH of 7 containing 200 μg/mL of lysozyme was assessed similarly. Magnetic nanoclusters were added (0.4 wt %) to the broth and a standard separation run was performed The lysozyme activities in the feed and unbound fraction were measured, indicating 25% binding of lysozyme. The lysozyme was eluted with 0.2M MgCl2 and 19% of the original lysozyme activity was recovered. Only about 4% of the cells were retained in the HGMS column with only a single column volume of wash buffer added, indicating that a protein can indeed be recovered from whole cell broth as a relatively pure component in a single step.

Example 8

Virus Clearance with Magnetic Nanoclusters

In Example 7 it was found that nanoclusters bind to cells, even at conditions where the overall cell charge repulses the nanocluster. A simple model based on the interaction energy between a protruding protein on the cell surface and a nanocluster was developed, and it was shown that nanoclusters can bind to cells at conditions where larger micron sized chromatography beads do not. While this is a negative result for protein separations in whole cell broth, it may prove useful in cases where binding of an entity with an overall charge that repulses the nanocluster is desired. Here the example of virus removal via protein binding on the viral surface is examined for both nanoclusters and for traditional chromatography beads.

Unlike the model in Example 7, the goal here was to quantitatively predict the fraction of viral particles bound to nanoclusters. Rather than calculate the overall energy as in Example 7, the known equilibrium binding of free protein is modified by the electrostatic repulsion of the nanocluster and like-charged viral surface.

The repulsion energy is:

$$u_e = 4\pi\varepsilon\varepsilon_0\left(\frac{R_vR_c}{R_v+R_c}\right)(\psi^\infty)^2\ln(1+\exp(-\kappa s)) \quad (1)$$

where s is the surface separation distance between the particles, $\psi^\infty$ is the surface potential of an isolated particle, which is approximately the zeta potential of the particle, κ is the inverse Debye length, ∈ is the dielectric constant, and $\in_0$ is the permitivity of free space and $R_v$ is the virus diameter and $R_c$ are the cluster diameter. With this repulsion energy, the relative affinity of the particle for a free protein and a protein on the surface can be found by setting s equal to the radius of the protein.

The overall reaction for protein binding is:

$$P_s + zI_b \Leftrightarrow P_b + zI_s \quad (2)$$

where P is the protein, I are the ions exchanged, z is the number of ions exchanged, the subscript s is for protein or ions in solution, and the subscript b is for the bound species. The equilibrium constant for free protein (not on the viral surface) is thus:

$$K_f = \frac{[P_b][I_s]^z}{[I_b]^z[P_s]}$$ (3)

and the ratio of the bound protein to the free protein is:

$$\frac{[P_b]}{[P_s]} = K_f \left(\frac{[I_b]}{[I_s]}\right)^z$$ (4)

For the rest of the analysis, it is assumed that the ionic strength is high and the fraction of the nanocluster surface covered by bound protein is small enough that binding does not change the ion concentrations significantly. Thus the ratio of the bound protein to the free protein is proportional to the equilibrium constant.

Assuming that the free energy of binding for the viral protein and the nanocluster is simply the free energy of binding of the free protein and the nanocluster plus the electrostatic interaction, it is possible to estimate the fraction of viral protein bound from the fraction of free protein bound under the same conditions:

$$K_f = \exp\left(-\frac{\Delta G_b}{kT}\right)$$ (5)

The equilibrium constant for the protein on the viral surface is:

$$K_v = \exp\left(-\frac{\Delta G_b + u_e}{kT}\right)$$ (6)

where $u_c$ can be found from equation 1. The ratio of the equilibrium constants and thus the ratio of the bound/free protein on the virus as compared to the free protein is:

$$\frac{K_v}{K_f} = \frac{\left(\frac{P_b}{P_s}\right)_v}{\left(\frac{P_b}{P_s}\right)_f} = \exp\left(-\frac{u_e}{kT}\right)$$ (7)

The ratio of free (mg/mL) to bound protein (mg/$g_{particles}$) at low nanocluster coverage is known at ionic strengths of 0.2 and 0.4 to be 0.83 and 0.15, respectively from the drosomycin and cytochrome-c binding isotherms. It is assumed that the ionic strength of the environment is 0.3 M. Assuming that the equilibrium constant is a linear function of $I^{0.5}$, the ratio of bound to unbound protein in solution is 0.45.

Since the virus has many proteins on the surface, but only one nanocluster needs to bind to the virus, the fraction of virus that has no nanoclusters bound is:

$$V_t/V_{tot} = [(P_t/P_{tot})_v]^n$$ (8)

Thus the viral clearance in log reduction is:

$$C = -\log(V_t/V_{tot})$$ (9)

With these models, the log reduction can be calculated from a simple electrostatic model and known equilibria for adsorption of proteins from free solution.

The first step in modeling the binding between a virus and a nanocluster is to estimate several important parameters. As a base case, the diameter of the virus was set at 100 nm, the diameter of the protein at 4 nm, the fraction of the surface that is protein at 2%, the magnetic nanocluster concentration at 0.1 wt %, the ionic strength at 0.3M with the nanocluster size 20, 50 and 100 nm, and the size of the chromatography bead set at 100 μm. All these parameters were then varied from this base case. In all cases, the virus, nanocluster and chromatography bead have a zeta potential of −30 mV.

Since this analysis is primarily to see if nanocluster binding is more favorable than traditional chromatography, the first variable explored was particle diameter, as shown in FIG. 11. Since the protein binding is unaffected by the particle size, but electrostatic repulsion is increased as the particle size increases, the log reduction is much higher with smaller nanoparticles. The lower size explored was 20 nm, which represents a single nanoparticle. While 20 nm magnetite particles cannot be captured by HGMS, it is possible, in other embodiments of this invention, to use nanoparticles comprised of cobalt-ferrite or iron, which can be captured as single nanoparticles.

Since the size of the virus can vary quite a bit, the effect of virus size was also modeled, as shown in FIG. 12. As the virus size increased, the total number of proteins on the surface increased, which increased n in equation 8 and increased the virus clearance. However, when chromatography beads were used, the electrostatic repulsion was roughly proportional to the size of the virus, and as the virus size increased the equilibrium constant dropped. With chromatography beads, there was a trade off in virus size, and a maximum viral clearance was found at about 70 nm. The nanoclusters were nearly the same size as the virus, and increasing virus size does not drastically increase the electrostatic repulsion, and larger viruses can be cleared more easily.

As the magnetic nanocluster concentration is increased, the fraction of bound protein increased, which increases viral binding. While viral clearance increases, the amount of the free protein bound also increases, so a trade off is expected. All calculations were conducted assuming that the binding sites on the nanoclusters were much higher than the total bound protein. When high free protein concentrations are present, this approximation will break down and the binding at high coverage will need to be calculated. However, the basic principle that as magnetic nanoparticle concentration is increased, more of the protein and virus are bound is generally true (FIG. 13).

The preceding calculations indicated that virus can indeed be bound by magnetic nanoclusters at conditions where column chromatography fails.

Nanocluster bound virus however, is with other proteins. What is needed is a means to bind the virus without binding free protein, or binding both but preferentially eluting free protein.

When the ionic strength dependence of viral binding is calculated, however, even when purely ionic binding is assumed (i.e. no hydrophobic interactions), the binding of virus increases as the ionic strength increases, while the fraction of free protein bound falls dramatically. This is due to the electrostatic repulsion, which is decreased by increasing ionic strength.

Thus at 0.3M ionic strength, greater than 99.9% of 100 nm viruses are bound to 50 nm nanoclusters, while less than 30% of the free protein is bound, due to multiple interactions with the nanocluster. Thus if binding is performed at 0.3M, a 3-log reduction of virus can be obtained while 70% of the protein is unbound. If the nanoclusters are eluted with 0.3M NaCl repeatedly, only 0.1% of the virus will be lost, but 70% of the protein will be recovered, and after several such elutions, nearly all the virus will be captured but nearly all the protein will be eluted (FIG. 14).

Figure 16:
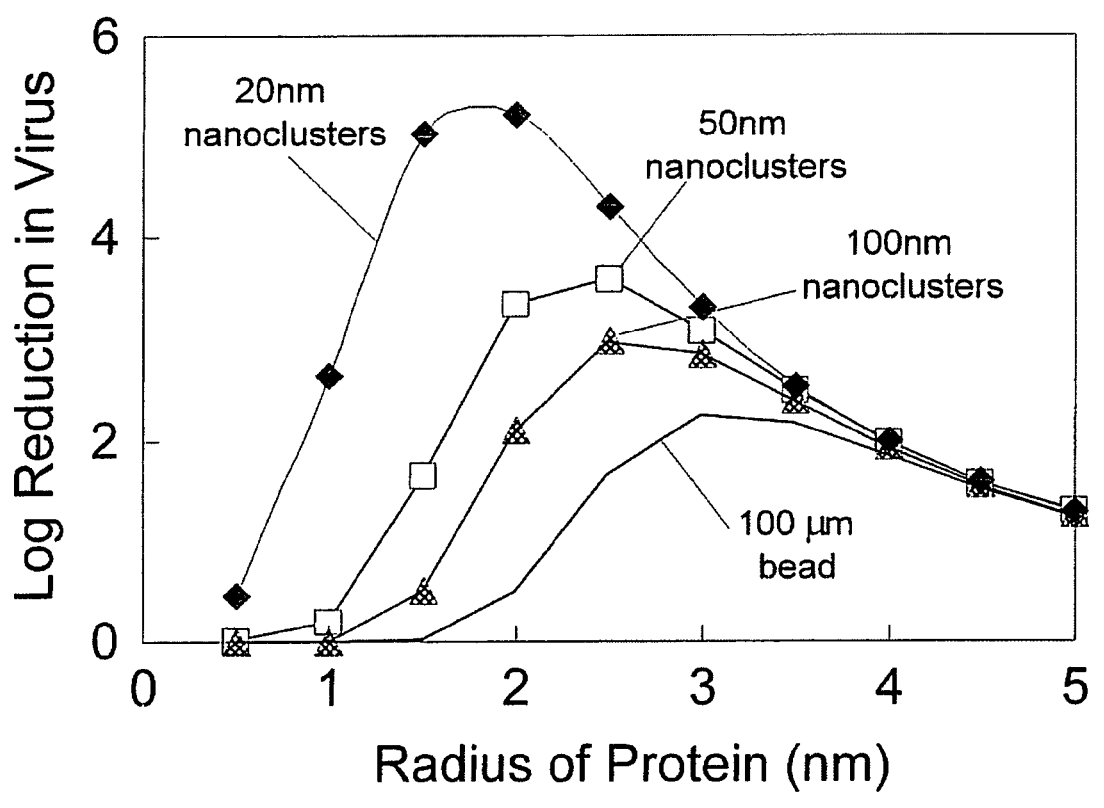

The effect of the other estimated parameters was performed, as shown in FIGS. 15 and 16. As the fraction of the surface that is protein increases, viral clearance increases. As the protein on the surface becomes larger at a constant fractional surface coverage, the protein protrudes from the surface further, and thus the electrostatic repulsion decreases, however, the total number decreases and the clearance decreases.

Based on the results of the model, one embodiment of the separation process may be as follows:
1. Add the magnetic nanoclusters to the protein and virus mixture
2. Pass the solution through HGMS
3. Wash the column with high ionic strength (~0.3M NaCl) until protein is no longer eluted
4. Elute the nanoclusters with high pH, low ionic strength to remove the virus.

In one embodiment of this separation process, there are no hydrophobic interactions between the protein and the nanocluster, and thus high ionic strength buffer elutes the protein. The nanoparticles according to this aspect are made with polymers that have no hydrophobic domains. Thus, for example, vinylsulfonic acid/acrylic acid copolymers may be used and the PEO shell will have no PPO.

What is claimed is:

1. A coloidally stable multi-polymer-coated magnetic nanocluster, comprising:
   a. a cluster of super paramagnetic core particles comprising a first polymer attached to said super paramagnetic core particles, wherein said first polymer coats said super paramagnetic core particles; wherein said coating of super paramagnetic core particle with said first polymer provides colloidally unstable cluster of super paramagnetic core particles and wherein said first polymer is selected from the group consisting of (i) a copolymer comprising acrylic acid and either or both of styrene sulfonic acid and vinyl sulfonic acid, (ii) a copolymer comprising acrylic acid and either or both of vinylbenzyl trimethyl ammonium chloride and acrylamidopropyl trimethyl ammonium chloride and (iii) a graft copolymer with a backbone of acrylic acid and side chain comprising either of both of polyethylene oxide and polypropylene oxide; and
   b. a second polymer attached to said cluster of super paramagnetic particles, wherein said second polymer comprises acrylic acid and is a discrete polymer chain from said first polymer and wherein said second polymer coats said cluster of super paramagnetic particles;
      wherein coating of said nanocluster with said second polymer renders said multi-polymer-coated magnetic nanocluster colloidally stable; and
   wherein said attachment of said super paramagnetic core particles to said first polymer and said attachment of said cluster of super paramagnetic core particles to said second polymer comprises a strong or weak interaction between said super paramagnetic core and said first polymer and between said cluster of super paramagnetic core particles and said second polymer; and
wherein said multi-polymer-coated magnetic nanocluster ranges in size from 20-1000 nm; and
   wherein said multi-polymer-coated magnetic nanocluster is stable in solutions of high and/or low ionic strength.

2. The multi-polymer-coated magnetic nanocluster of claim 1, wherein said super paramagnetic core particles comprise magnetite.

3. The multi-polymer-coated magnetic nanocluster of claim 1, wherein said nanocluster ranges in size from 35-200 nm.

4. The multi-polymer-coated magnetic nanocluster of claim 1, wherein said nanocluster size is controlled via limiting the amount of polymer 1.

5. The multi-polymer-coated magnetic nanocluster of claim 1, wherein said first polymer comprises acrylic acid, styrene sulfonic acid, vinyl sulfonic acid, vinyl benzyl trimethyl ammonium chloride, acrylamidopropyl trimethyl ammonium chloride, polyethylene oxide or polypropylene oxide or polyacrylic acid, or any combination thereof.

6. The multi-polymer-coated magnetic nanocluster of claim 1, wherein said first polymer comprises acrylic acid, styrene sulfonic acid and vinyl sulfonic acid.

7. The multi-polymer-coated magnetic nanocluster of claim 6, wherein the concentration of said vinyl sulfonic acid ranges from 25-50%.

8. The multi-polymer-coated magnetic nanocluster of claim 6, wherein the concentration of said styrene sulfonic acid ranges from 25-75%.

9. The multi-polymer-coated magnetic nanocluster of claim 6, wherein the concentration of said acrylic acid is roughly 25%.

10. The multi-polymer-coated magnetic nanocluster of claim 6, wherein the ratio of said acrylic acid concentration to iron atom concentration ranges from 0.1-0.6.

11. The multi-polymer-coated magnetic nanocluster of claim 6, wherein the ratio of said acrylic acid concentration to iron atom concentration is 0.2.

12. The multi-polymer-coated magnetic nanocluster of claim 1, wherein said first polymer comprises vinyl benzyl trimethyl ammonium chloride or acrylamidopropyl trimethyl ammonium chloride and acrylic acid.

13. The multi-polymer-coated magnetic nanocluster of claim 12, wherein the concentration of said vinyl benzyl trimethyl ammonium chloride or acrylamidopropyl trimethyl ammonium chloride ranges from 25-90%.

14. The multi-polymer-coated magnetic nanocluster of claim 12, wherein the concentration of said vinyl benzyl trimethyl ammonium chloride or acrylamidopropyl trimethyl ammonium chloride ranges from 70-80%.

15. The multi-polymer-coated magnetic nanocluster of claim 12, wherein the concentration of said acrylic acid is roughly 75%.

16. The multi-polymer-coated magnetic nanocluster of claim 12, wherein the ratio of said acrylic acid concentration to iron atom concentration ranges from 0.1-0.6.

17. The multi-polymer-coated magnetic nanocluster of claim 12, wherein the ratio of said acrylic acid concentration to iron atom concentration is 0.2.

18. The multi-polymer-coated magnetic nanocluster of claim 1, wherein said first polymer is a copolymer, comprising polyethylene oxide and polypropylene oxide grafted on polyacrylic acid and wherein said second polymer is polyacrylic acid.

19. The multi-polymer-coated magnetic nanocluster of claim 18, wherein said polyethylene oxide is grafted at a concentration of 8-16%.

20. The multi-polymer-coated magnetic nanocluster of claim 18, wherein said polyethylene oxide is grafted at a concentration of 0-8%.

21. The multi-polymer-coated magnetic nanocluster of claim 18, wherein said polyacrylic acid has a molecular weight of 5000.

22. The multi-polymer-coated magnetic nanocluster of claim 18, wherein the concentration of said polymer is 0.25-1.25 grams of polymer per gram of magnetite.

23. The multi-polymer-coated magnetic nanocluster of claim 18, wherein the concentration of polymer is at a concentration of 0.25 grams of polymer per gram of magnetite.

24. The multi-polymer-coated magnetic nanocluster of claim 1, wherein said second polymer comprises acrylic acid, vinyl sulfonic acid, vinyl benzyl trimethyl ammonium chloride, acrylamidopropyl trimethyl ammonium chloride, polyethylene oxide, polypropylene oxide or polyacrylic acid, or any combination thereof.

25. The multi-polymer-coated magnetic nanocluster of claim 1, wherein said second polymer is less than 15 kilodalton in size.

26. The multi-polymer-coated magnetic nanocluster of claim 18, wherein said poly acrylic acid has a molecular weight of 2,000-250,000.

27. The multi-polymer-coated magnetic nanocluster of claim 18, wherein said poly acrylic acid has a molecular weight of 5,000.

28. The multi-polymer-coated magnetic nanocluster of claim 18, wherein the concentration of said polymer ranges from 0.1-0.5 grams of polymer per gram of magnetite.

29. The multi-polymer-coated magnetic nanocluster of claim 18, wherein the concentration of polymer is at a concentration of 0.3 grams of polymer per gram of magnetite.

30. The multi-polymer-coated magnetic nanocluster of claim 1, wherein said second polymer comprises a copolymer of acrylic acid and vinyl sulfonic acid.

31. The multi-polymer-coated magnetic nanocluster of claim 30, wherein the concentration of said acrylic acid and vinyl sulfonic acid ranges from 25-50%.

32. The multi-polymer-coated magnetic nanocluster of claim 30, wherein the concentration of said acrylic acid and vinyl sulfonic acid is roughly 25%.

33. The multi-polymer-coated magnetic nanocluster of claim 30, wherein the concentration of polymer is at a concentration ranging from 0.1-0.5 grams of polymer per gram of magnetite.

34. The multi-polymer-coated magnetic nanocluster of claim 30, wherein the concentration of polymer is at a concentration of 0.4 grams of polymer per gram of magnetite.

35. The multi-polymer-coated magnetic nanocluster of claim 1, wherein said second polymer stabilizes said multi-polymer-coated magnetic nanocluster by creating a steric shell around said nanocluster.

36. The multi-polymer-coated magnetic nanocluster of claim 1, wherein said second polymer stabilizes said multi-polymer-coated magnetic nanocluster by providing a charge to said multi-polymer-coated magnetic nanocluster.

37. The multi-polymer-coated magnetic nanocluster of claim 1, wherein said first polymer comprises styrene sulfonic acid, vinyl sulfonic acid and acrylic acid, and said second polymer comprises polyethylene oxide and propylene oxide grafted on polyacrylic acid, or polyacrylic acid, or acrylic acid and vinyl sulfonic acid.

38. The multi-polymer-coated magnetic nanocluster of claim 1, wherein said first polymer comprises vinyl benzyl trimethyl ammonium chloride or acrylamidopropyl trimethyl ammonium chloride and acrylic acid, and said second polymer comprises vinyl benzyl trimethyl ammonium chloride or acrylamidopropyl trimethyl ammonium chloride and acrylic acid.

39. The multi-polymer-coated magnetic nanocluster of claim 1, wherein said first polymer comprises polyethylene oxide and polypropylene oxide grafted on polyacrylic acid, and said second polymer comprises polyethylene oxide and polypropylene oxide grafted on polyacrylic acid, or polyacrylic acid, or polymer of acrylic acid and vinyl sulfonic acid.

40. The multi-polymer-coated magnetic nanocluster of claim 1, further comprising a targeting moiety.

41. The multi-polymer-coated magnetic nanocluster of claim 40, wherein said targeting moiety is Protein A or Protein G.

42. A solution comprising the multi-polymer-coated magnetic nanocluster of claim 1.

43. The solution of claim 42, wherein said solution is an aqueous solution.

44. The solution of claim 42, wherein said solution is of high ionic strength.

* * * * *